(12) United States Patent
Okuda

(10) Patent No.: US 10,448,827 B2
(45) Date of Patent: Oct. 22, 2019

(54) OPHTHALMOLOGIC IMAGING APPARATUS

(71) Applicant: KABUSHIKI KAISHA TOPCON, Itabashi-ku, Tokyo (JP)

(72) Inventor: Youki Okuda, Tokyo (JP)

(73) Assignee: KABUSHIKI KAISHA TOPCON, Itabashi-ku, Tokyo (JP)

( * ) Notice: Subject to any disclaimer, the term of this patent is extended or adjusted under 35 U.S.C. 154(b) by 46 days.

(21) Appl. No.: 15/575,850

(22) PCT Filed: Jan. 19, 2016

(86) PCT No.: PCT/JP2016/051469
§ 371 (c)(1),
(2) Date: Nov. 21, 2017

(87) PCT Pub. No.: WO2016/189890
PCT Pub. Date: Dec. 1, 2016

(65) Prior Publication Data
US 2018/0125361 A1 May 10, 2018

(30) Foreign Application Priority Data
May 26, 2015 (JP) .................................. 2015-106084

(51) Int. Cl.
*A61B 3/12* (2006.01)
*A61B 3/14* (2006.01)
(Continued)

(52) U.S. Cl.
CPC ................ *A61B 3/14* (2013.01); *A61B 3/102* (2013.01); *A61B 3/12* (2013.01); *G03B 13/36* (2013.01);
(Continued)

(58) Field of Classification Search
CPC .... A61B 3/14; A61B 3/10; A61B 3/12; A61B 3/102; A61B 3/0058; A61B 3/0075; G03B 13/36; G03B 17/48
(Continued)

(56) References Cited

U.S. PATENT DOCUMENTS 8,749,795 B2 * 6/2014 Sugita ................ G01B 9/02044
356/479
9,706,919 B2 * 7/2017 Ota .......................... A61B 3/14
(Continued)

FOREIGN PATENT DOCUMENTS

JP 2010-193987 A 9/2010
JP 2011-189063 A 9/2011
(Continued)

OTHER PUBLICATIONS

International Search Report dated Mar. 1, 2016, in connection with International Patent Application No. PCT/JP2016/051469, 3 pgs.

*Primary Examiner* — William R Alexander
(74) *Attorney, Agent, or Firm* — Chiesa Shahinian & Giantomasi PC

(57) ABSTRACT

An ophthalmologic imaging apparatus that includes a first optical system, a first driver, and a first focus controller. The first optical system includes a first focus lens and a diopter correction lens, and guides light from a subject's eye to a first light receiving element. The first focus lens is movable along the optical axis of a first optical path. The diopter correction lens is insertable into and removable from the first optical path. The first driver moves the first focus lens. The first focus controller executes mutually different focus control of the first driver in a removed state in which the first diopter correction lens is removed from the first optical path and in an inserted state in which the diopter correction lens is inserted into the first optical path.

19 Claims, 10 Drawing Sheets

(51) Int. Cl.
   *A61B 3/10*     (2006.01)
   *G03B 13/36*   (2006.01)
   *A61B 3/00*     (2006.01)
   *G03B 17/48*   (2006.01)

(52) U.S. Cl.
   CPC .......... *A61B 3/0058* (2013.01); *A61B 3/0075* (2013.01); *G03B 17/48* (2013.01)

(58) Field of Classification Search
   USPC ........................................................ 351/206
   See application file for complete search history.

(56) References Cited

U.S. PATENT DOCUMENTS

| | | | |
|---|---|---|---|
| 2009/0244483 A1 | 10/2009 | Yoshino et al. | |
| 2011/0267583 A1* | 11/2011 | Hayashi ............. | G01B 9/02028 351/206 |
| 2011/0292339 A1 | 12/2011 | Itoh | |
| 2012/0293807 A1* | 11/2012 | Sugita ................ | G01B 9/02044 356/479 |
| 2013/0301006 A1* | 11/2013 | Kim ...................... | A61B 3/102 351/206 |
| 2014/0118689 A1 | 5/2014 | Saito et al. | |
| 2014/0132930 A1 | 5/2014 | Ogura | |
| 2014/0354950 A1* | 12/2014 | Buckland ............... | A61B 3/102 351/206 |

FOREIGN PATENT DOCUMENTS

| | | |
|---|---|---|
| JP | 2011-245137 A | 12/2011 |
| JP | 2014-083396 A | 5/2014 |
| JP | 2014-094141 A | 5/2014 |

* cited by examiner

FIG. 4

| POSITION OF FOCUS OPTICAL SYSTEM | POSITION OF PHOTOGRAPHY FOCUS LENS |
|---|---|
| F1 | D1 |
| F2 | D2 |
| . | . |
| . | . |
| . | . |

FIG. 5

| POSITION OF OCT FOCUS LENS | POSITION OF PHOTOGRAPHY FOCUS LENS |
|---|---|
| C1 | d1 |
| C2 | d2 |
| . | . |
| . | . |
| . | . |

OPHTHALMOLOGIC IMAGING APPARATUS

CROSS-REFERENCE TO RELATED APPLICATIONS

This application is a national stage (under 35 U.S.C. 371) of International Patent Application No. PCT/JP2016/051469, filed Jan. 19, 2016, claiming priority to Japanese Patent Application No. 2015-106084, filed May 26, 2015, both of which are herein incorporated by reference in their entirety.

FIELD

Embodiments described herein relate to an ophthalmologic imaging apparatus.

BACKGROUND

Ophthalmologic imaging apparatuses for photographing subject's eyes are known from the past. An ophthalmologic imaging apparatus includes, for example, an illumination optical system that projects an illumination light beam onto a subject's eye and an imaging optical system that guides reflection light from the fundus to an imaging device. Some of such ophthalmologic imaging apparatuses have an autofocus function that changes the focus position of the imaging optical system by projecting two split indicators onto the fundus of the subject's eye and moving the focus lens based on the positional relationship between two split indicator images acquired by the returning light from the fundus.

In an ophthalmologic imaging apparatus with the autofocus function, a focusable range by the movement of the focus lens is set to be a range in which diopter of an average subject's eye is correctable. Accordingly, there are cases in which the focus position of the imaging optical system cannot be determined even when the focus lens is moved with respect to a subject's eye with high myopia or with high hyperopia. Therefore, in order to enable performing focus adjustment for subject's eyes with high myopia or with high hyperopia with the focus lens, a diopter correction lens is inserted into the optical path of the imaging optical system.

However, when the diopter correction lens has been inserted into the optical path of the imaging optical system, the optical relationship between the imaging optical system and the focus optical system that projects the split indicators onto the fundus changes, and the split indicator images cannot be acquired by the imaging optical system. As a result, not only automatic focusing by the autofocus function but also manual focusing using the split indicators becomes impossible.

For example, Patent Document 1 proposes a technique in which manual focusing can be smoothly performed in a state where the diopter correction lens has been inserted into the optical path by moving the focus lens in such a way that a moving speed for the case where the diopter correction lens has been inserted into the optical path is faster than a moving speed for the case where the diopter correction lens has been removed.

Japanese Unexamined Patent Application Publication No. 2011-189063

However, in the ophthalmologic imaging apparatus disclosed in Patent Document 1, focus adjustment cannot be performed automatically when the diopter correction lens has been inserted into the optical path of the imaging optical system. This requires long time for those who are unfamiliar with the apparatus to perform adjustment of the focus position, and it becomes difficult to perform focusing with high precision.

SUMMARY

The present invention is made for solving the aforementioned problem, and the object thereof is to provide an ophthalmologic imaging apparatus that is capable of performing automatic focusing on and photographing a subject's eye even in the case where a diopter correction lens has been inserted into an optical path.

An ophthalmologic imaging apparatus of an embodiment includes a first optical system, a first driver, and a first focus controller. The first optical system includes a first focus lens and a diopter correction lens, and guides light from a subject's eye to a first light receiving element. The first focus lens is movable along the optical axis of a first optical path. The diopter correction lens is insertable into and removable from the first optical path. The first driver moves the first focus lens. The first focus controller executes mutually different focus control of the first driver in a removed state in which the first diopter correction lens is removed from the first optical path and in an inserted state in which the diopter correction lens is inserted into the first optical path.

According to the present invention, it is possible to provide an ophthalmologic imaging apparatus that is capable of automatically focusing on and photographing a subject's eye even in the case where a diopter correction lens has been inserted into an optical path.

BRIEF DESCRIPTION OF THE DRAWINGS

FIG. 4 is a schematic diagram illustrating an example of the configuration of the control system of the ophthalmologic imaging apparatus according to the embodiment.

FIG. 5 is a schematic diagram illustrating an example of the configuration of the control system of the ophthalmologic imaging apparatus according to the embodiment.

DETAILED DESCRIPTION

An exemplary embodiment of the present invention will be described in detail with reference to the drawings. The ophthalmologic imaging apparatus according to the embodiment includes a first optical system and a second optical system. The first optical system can change a focus position and is for photographing a subject's eye. The second optical system can change a focus position separately from the first optical system and is for observation or photography of the subject's eye. The first optical system includes a diopter correction lens that can be inserted into and removed from an optical path. The focus position of the first optical system in which the diopter correction lens has been inserted into the optical path can be changed on the basis of the control content of the focus control executed for the subject's eye by the second optical system.

Hereinafter, the ophthalmologic imaging apparatus according to the embodiment includes two optical systems each capable of photographing the subject's eye. As a specific example, the ophthalmologic imaging apparatus according to the embodiment has a function of a fundus photographing device and a function of optical coherence tomography, and performs fundus photography and optical coherence tomography (hereinafter referred to as OCT) of the subject's eye. This OCT is performed for an arbitrary site of the subject's eye such as the fundus and the anterior segment.

The ophthalmologic imaging apparatus described in the following embodiment is capable of performing Fourier domain OCT. In particular, the ophthalmologic imaging apparatus according to the embodiment can perform swept source OCT technique. It should be noted that the configuration according to the present invention can also be applied to an ophthalmologic imaging apparatus capable of performing OCT of a type other than the swept source type, for example a spectral domain type. In addition, the following embodiment describes an apparatus in which a fundus camera (or a retinal camera) having a fundus photography function and an OCT apparatus are combined. However, it is also possible to combine a fundus camera that has the configuration according to the embodiment to a modality other than the OCT apparatus, for example, a scanning laser ophthalmoscope (SLO), a slit lamp microscope, an ophthalmic surgical microscope, a photocoagulation apparatus, or the like.

In this specification, images acquired using OCT may be collectively referred to as OCT images. In addition, the contents of the documents cited in this specification can be incorporated as contents of the following embodiment.

[Configuration]

Figure 1:
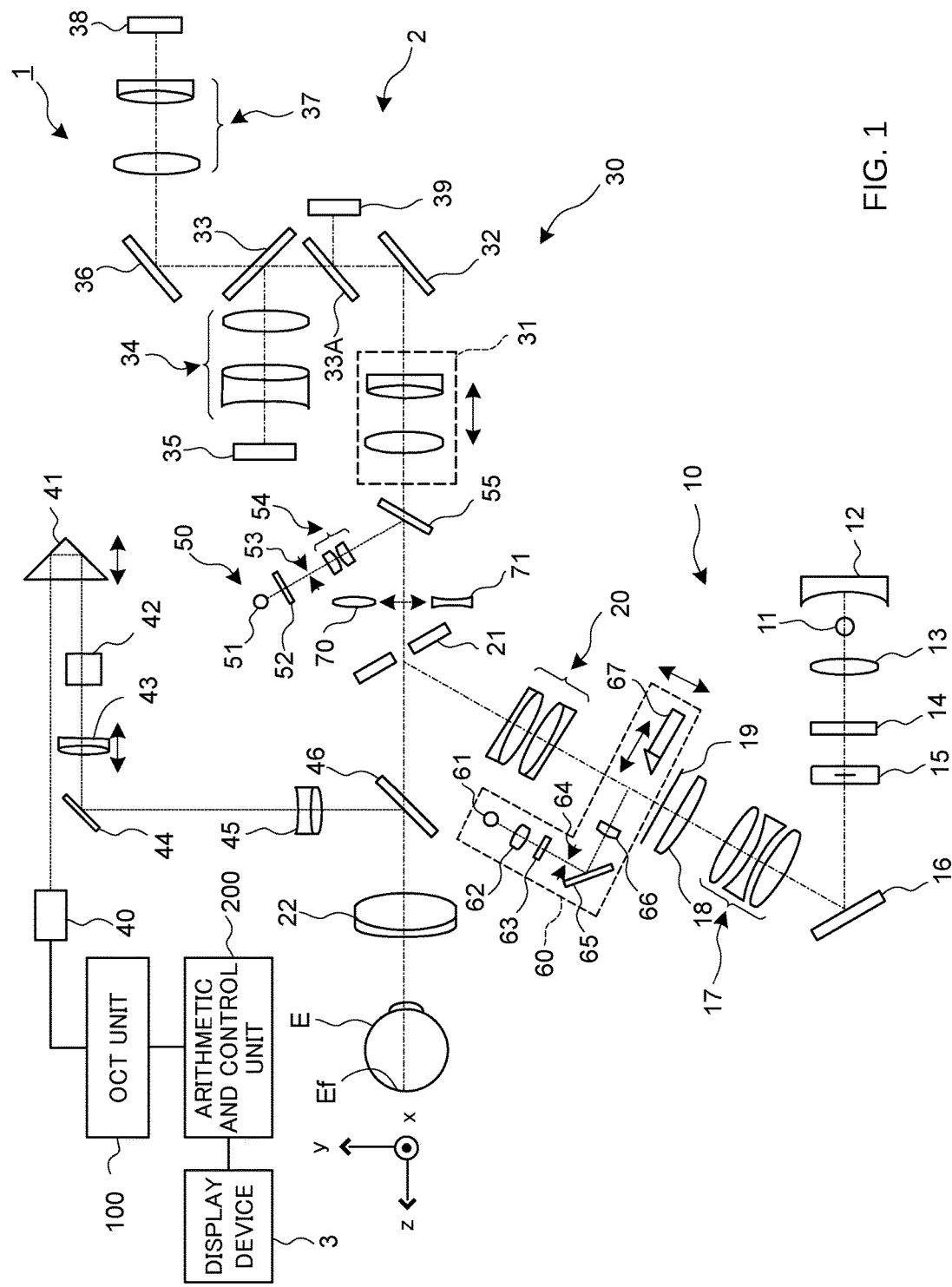
FIG. 1 is a schematic diagram illustrating an example of a configuration of an optical system of an ophthalmologic imaging apparatus according to an embodiment.

As shown in FIG. 1, the ophthalmologic imaging apparatus 1 includes the fundus camera unit 2, the OCT unit 100, and the arithmetic and control unit 200. The fundus camera unit 2 has substantially the same optical system as the conventional fundus camera. The OCT unit 100 is provided with an optical system for performing OCT. The arithmetic and control unit 200 is provided a computer(s) that executes various kinds of arithmetic processing, control processing, and the like.

[Fundus Camera Unit]

The fundus camera unit 2 shown in FIG. 1 is provided with an optical system for acquiring two dimensional images (fundus images) rendering the surface morphology of the fundus Ef of the subject's eye E. Examples of the fundus images include observation images and photographed images. An observation image is, for example, a monochrome moving image formed at a predetermined frame rate using near-infrared light. A photographed image is, for example, a color image captured by flashing visible light, or a monochrome still image captured using near-infrared light or visible light as illumination light. The fundus camera unit 2 may be configured to be capable of acquiring other types of images such as fluorescein angiograms, indocyanine green angiograms, and autofluorescent images.

The fundus camera unit 2 is provided with a jaw holder and a forehead rest for supporting the face of the subject. In addition, the fundus camera unit 2 is provided with the illumination optical system 10 and the photographing optical system 30. The illumination optical system 10 projects illumination light onto the fundus Ef. The photographing optical system 30 guides the illumination light reflected from the fundus Ef to an imaging device (i.e., the CCD image sensor 35 or 38). Each of the CCD image sensors 35 and 38 is sometimes simply referred to as a "CCD". Further, the photographing optical system 30 guides measurement light coming from the OCT unit 100 to the subject's eye E, and guides the measurement light returning from the subject's eye E to the OCT unit 100.

The observation light source 11 of the illumination optical system 10 includes, for example, a halogen lamp or a light emitting diode (LED). The light (observation illumination light) output from the observation light source 11 is reflected by the reflection mirror 12 having a concave reflective surface, passes through the condenser lens 13, and becomes near-infrared light after passing through the visible cut filter 14. Further, the observation illumination light is once converged near the photographing light source 15, reflected by the mirror 16, and passes through the relay lenses 17 and 18, the diaphragm 19, and the relay lens 20. Then, the observation illumination light is reflected on the peripheral part (the surrounding area of the aperture part) of the aperture mirror 21, penetrates the dichroic mirror 46, and refracted by the objective lens 22, thereby illuminating the fundus Ef.

The observation illumination light reflected from the fundus Ef is refracted by the objective lens 22, penetrates the dichroic mirror 46, passes through the aperture part formed in the center area of the aperture mirror 21, passes through the dichroic mirror 55, travels through the photography focus lens 31, and is reflected by the mirror 32. Further, the fundus reflection light passes through the half mirror 33A, is reflected by the dichroic mirror 33, and forms an image on the light receiving surface of the CCD image sensor 35 by the condenser lens 34. The CCD image sensor 35 detects the fundus reflection light at a predetermined frame rate, for example. An image (observation image) based on the fundus reflection light detected by the CCD image sensor 35 is displayed on the display device 3. Note that when the focus of the photographing optical system 30 is adjusted to the anterior segment of the subject's eye E, an observation image of the anterior segment of the subject's eye E is acquired and displayed.

The photographing light source 15 is formed of, for example, a xenon lamp or an LED. The light (photographing illumination light) output from the photographing light source 15 is guided to the fundus Ef along the same route as that of the observation illumination light. The photographing illumination light reflected from the fundus Ef is guided to the dichroic mirror 33 along the same route as that of the observation illumination light, passes through the dichroic mirror 33, is reflected by the mirror 36, and forms an image on the light receiving surface of the CCD image sensor 38 by the condenser lens 37. The display device 3 displays an image (photographed image) based on the fundus reflection light detected by the CCD image sensor 38. Note that the same device or different devices may be used for the display device 3 for displaying observation images and the display device 3 for displaying photographed images. Besides, when similar photography is performed by illuminating the subject's eye E with infrared light, an infrared photographed image is displayed. It is also possible to use an LED as a photographing light source.

The liquid crystal display (LCD) 39 displays a fixation target and a visual target used for visual acuity test. The fixation target is a visual target for fixating the subject's eye E, and is used when performing fundus photography and OCT measurement.

Part of the light output from the LCD 39 is reflected by the half mirror 33A, reflected by the mirror 32, travels through the photography focus lens 31 and the dichroic mirror 55, and passes through the aperture part of the aperture mirror 21. The light passed through the aperture part of the aperture mirror 21 penetrates the dichroic mirror 46, and is refracted by the objective lens 22, thereby being projected onto the fundus Ef. By changing the display position of the fixation target on the screen of the LCD 39, the fixation position of the subject's eye E can be changed.

In addition, as with a conventional fundus camera, the fundus camera unit 2 is provided with the alignment optical system 50 and the focus optical system 60. The alignment optical system 50 generates an indicator (alignment indicator) for performing the position adjustment (alignment) of the optical system with respect to the subject's eye E. The focus optical system 60 generates an indicator (split indicator) for adjusting the focus of the photographing optical system 30 with respect to the subject's eye E.

The light output from an LED 51 of the alignment optical system 50 (alignment light) travels through the diaphragms 52 and 53 and the relay lens 54, is reflected by the dichroic mirror 55, and passes through the aperture part of the aperture mirror 21. The alignment light passed through the aperture part of the aperture mirror 21 penetrates the dichroic mirror 46, and is projected onto the cornea of the subject's eye E by the objective lens 22.

The alignment light reflected from the cornea travels through the objective lens 22, the dichroic mirror 46 and the above-mentioned aperture part. Part of the cornea reflection light penetrates the dichroic mirror 55 and passes through the photography focus lens 31. The cornea reflection light passed through the photography focus lens 31 is reflected by the mirror 32, penetrates the half mirror 33A, is reflected by the dichroic mirror 33, and is projected onto the light receiving surface of the CCD image sensor 35 by the condenser lens 34. The received image (alignment indicator image) captured by the CCD image sensor 35 is displayed on the display device 3 together with the observation image. The user conducts an alignment operation in the same manner as performed on a conventional fundus camera. Instead, alignment may be performed in such a way that the arithmetic and control unit 200 analyzes the position of the alignment indicator image and moves the optical system (automatic alignment).

The focus optical system 60 is movable along the optical path of the illumination optical system 10 (hereinafter occasionally referred to as "illumination optical path") in conjunction with the movement of the photography focus lens 31 along the optical path of the photographing optical system 30 (hereinafter occasionally referred to as "photographing optical path"). The reflection rod 67 of the focus optical system 60 can be inserted and removed into and from the illumination optical path.

To conduct focus adjustment, the reflective surface of the reflection rod 67 is arranged in a slanted position on the illumination optical path. The light output from the LED 61 of the focus optical system 60 (i.e., focus light) passes through the relay lens 62, is split into two light beams by the split indicator plate 63, passes through the two-hole diaphragm 64. The focus light passed through the two-hole diaphragm 64 is reflected by the mirror 65, is converged on the reflective surface of the reflection rod 67 by the condenser lens 66, and is reflected by the reflective surface. Further, the focus light travels through the relay lens 20, is reflected by the aperture mirror 21, penetrates the dichroic mirror 46, and is refracted by the objective lens 22, thereby being projected onto the fundus Ef.

The focus light reflected from the fundus is guided along the same route as the alignment light reflected from the cornea and is detected by the CCD image sensor 35. The received image (split indicator image) captured by the CCD image sensor 35 is displayed on the display device 3 together with the observation image. As in the conventional case, the arithmetic and control unit 200 can analyze the position of the split indicator image, and move the photography focus lens 31 and the focus optical system 60 for the focus adjustment (automatic focusing). Instead, the user may manually perform the focus adjustment while visually checking the split indicator image.

The reflection rod 67 is inserted at a position on the illumination optical path, which is substantially optically conjugate with the fundus Ef of the subject's eye E. The position of the reflective surface of the reflection rod 67 inserted into the illumination optical path is a position substantially optically conjugate with the split indicator plate 63. As described above, the split indicator light beam is split into two beams by the action of the two-hole diaphragm 64 and the like. When the fundus Ef of the subject's eye E and the reflective surface of the reflection rod 67 are not conjugate with one another, two split indicator images acquired by the CCD image sensor 35 are displayed on the display device 3 in such a way that the split indicator images are separated in the right-and-left direction, for example. When the fundus Ef of the subject's eye E and the reflective surface of the reflection rod 67 are substantially optically conjugate with each other, the two split indicator images are displayed on the display device 3 in such a way that the positions of the split indicator images, which are arranged in the vertical direction, acquired by the CCD image sensor 35 match, for example. The focus optical system 60 is moved along the illumination optical path in conjunction with the movement of the photography focus lens 31 so that the fundus Ef and the split indicator plate 63 are always optically conjugate with each other. When the fundus Ef and the split indicator plate 63 are not conjugate with one another, the split indicator image is separated into two. Thus, the position of the photography focus lens 31 is obtained by moving the focus optical system 60 so that the two split indicator images, which are arranged in the vertical direction, match. although the present embodiment describes the case where two split indicator images are acquired, the number of split indicator images acquired may be three or more.

The photographing optical system 30 includes the diopter correction lenses 70 and 71 that can be inserted into and removed from a position in the photographing optical path between the aperture mirror 21 and the dichroic mirror 55. The diopter correction lens 70 is a plus (+) lens that is used to correct high hyperopia. For the diopter correction lens 70, for example, a convex lens of +20D (diopter) is used. The diopter correction lens 71 is a minus (−) lens which is used to correct high myopia. For the diopter correction lens 71, for example, a concave lens of −20D (diopter) is used. For example, the turret plate is provided with diopter correction lenses 70 and 71 along the circumferential direction. In addition, an aperture part is formed in the circumferential direction of the turret plate. The turret plate is rotated by a stepping motor (a driver) or the like around a rotation axis provided at a position decentered from the optical axis of the photographing optical system 30. By rotating the turret plate around the rotation axis with the stepping motor, it becomes possible to dispose the diopter correction lens 70 or the diopter correction lens 71 in the photographing optical path, and to remove the diopter correction lens 70 and/or the diopter correction lens 71 from the photographing optical path.

The dichroic mirror 46 branches the optical path for OCT from the optical path for fundus photography. The dichroic mirror 46 reflects light of wavelengths used for OCT, and transmits light used for fundus photography. The optical path for OCT is provided with, in order from the OCT unit 100 side, the collimator lens unit 40, the optical path length (OPL) changing unit 41, the optical scanner 42, the OCT focus lens 43, the mirror 44, and the relay lens 45.

The optical path length changing unit 41 is movable in directions indicated by the arrow in FIG. 1, thereby changing the length of the optical path for OCT measurement. The change in the optical path length is used for the correction of the optical path length according to the axial length of the subject's eye E, for the adjustment of the interference state, or the like. The optical path length changing unit 41 includes, for example, a corner cube and a mechanism for moving the corner cube.

The optical scanner 42 is disposed at a position optically conjugate with the pupil of the subject's eye E. The optical scanner 42 changes the traveling direction of light (measurement light LS) traveling along the OCT optical path. With this, the subject's eye E can be scanned with the measurement light LS. The optical scanner 42 includes, for example, a galvano mirror that deflects the measurement light LS in the x direction, a galvano mirror that deflects the measurement light LS in the y direction, and a mechanism(s) that independently drives the galvano mirrors. With this, it becomes possible to scan the measurement light LS in an arbitrary direction in the xy plane.

[OCT Unit]

Figure 2:
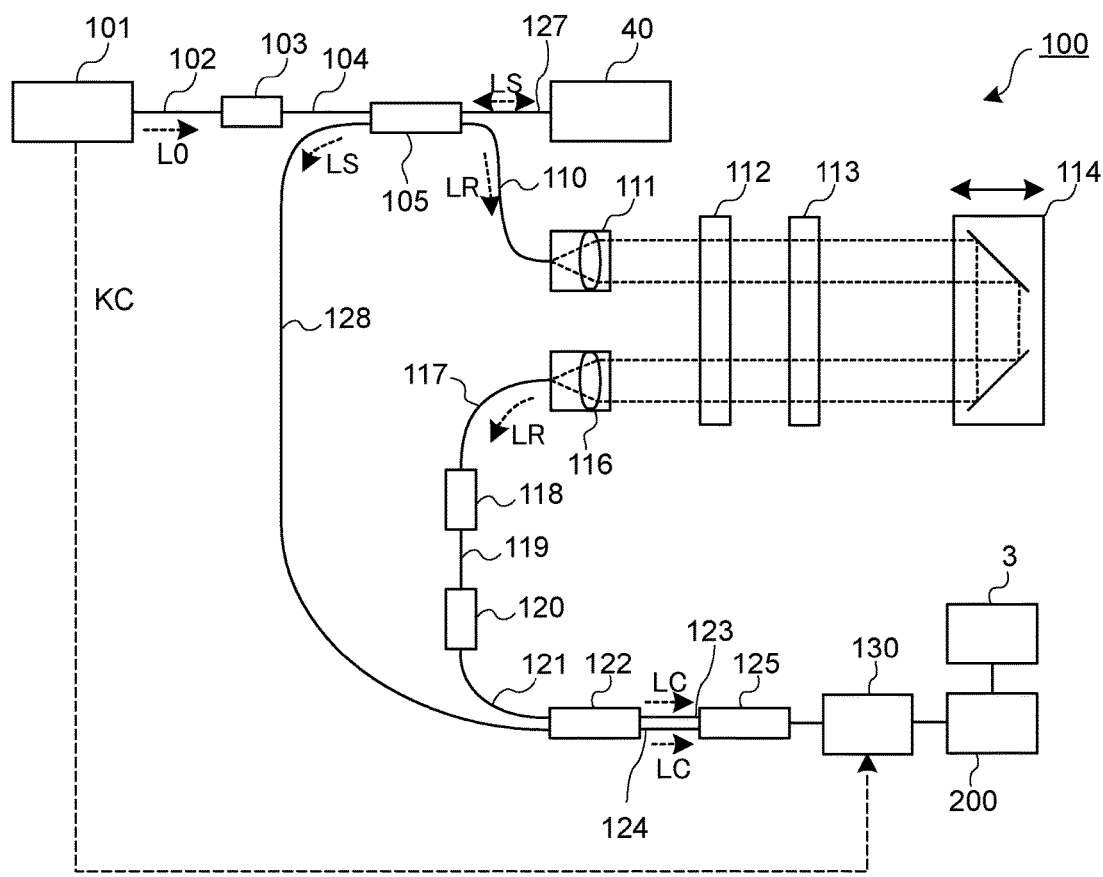
FIG. 2 is a schematic diagram illustrating an example of the configuration of the optical system of the ophthalmologic imaging apparatus according to the embodiment.

An example of the configuration of the OCT unit 100 is shown in FIG. 2. The OCT unit 100 includes an optical system for acquiring OCT images of the subject's eye E. The optical system has the same configuration as the conventional swept source OCT apparatus. That is, the optical system includes an interference optical system that splits light from a wavelength tunable type (wavelength scanning type) light source into measurement light and reference light, superposes the measurement light returning from the subject's eye E on the reference light having traveled through the reference optical path to generate interference light, and detects the interference light. The result of detection of the interference light obtained by the interference optical system (detection signal) is a signal indicating a spectrum of the interference light, and is sent to the arithmetic and control unit 200.

Like swept source OCT apparatuses commonly used, the light source unit 101 includes a wavelength tunable type (wavelength scanning type) light source capable of sweeping (scanning) the wavelengths of emitted light. The wavelength tunable type light source includes a laser light source that includes a resonator. The light source unit 101 temporally changes the output wavelengths within the near-infrared wavelength bands that cannot be visually recognized with human eyes.

The light L0 output from the light source unit 101 is guided to the polarization controller 103 through the optical fiber 102 and the polarization state thereof is adjusted. The polarization controller 103, for example, applies external stress to the looped optical fiber 102 to adjust the polarization state of the light L0 guided through the optical fiber 102.

The light L0 whose polarization state has been adjusted by the polarization controller 103 is guided to the fiber coupler 105 through the optical fiber 104, and is split into the measurement light LS and the reference light LR.

The reference light LR is guided to the collimator 111 through the optical fiber 110 and becomes a parallel light beam. The reference light LR, which has become a parallel light beam, is guided to the corner cube 114 via the optical path length correction member 112 and the dispersion compensation member 113. The optical path length correction member 112 acts as delay means for matching the optical path length (optical distance) of the reference light LR with the optical path length of the measurement light LS. The dispersion compensation member 113 acts as dispersion compensation means for matching the dispersion characteristics between the reference light LR and the measurement light LS.

The corner cube 114 reverses the traveling direction of the reference light LR that has become the parallel light beam by the collimator 111. The optical path of the reference light LR incident on the corner cube 114 and the optical path of the reference light LR emitted from the corner cube 114 are parallel to each other. Further, the corner cube 114 is movable in a direction along the incident light path and the emitting light path of the reference light LR. Through such movement, the length of the optical path of the reference light LR is varied.

The configuration shown in FIG. 1 and FIG. 2 includes both the optical path length changing unit 41 that changes the length of the optical path of the measurement light LS (i.e., measurement optical path or measurement arm) and the corner cube 114 that changes the length of the optical path of the reference light LR (i.e., reference optical path or reference arm). Alternatively, any one of the optical path length changing unit 41 and the corner cube 114 may be provided. The difference between the measurement optical path length and the reference optical path length may be changed using another kind of optical member.

The reference light LR that has traveled through the corner cube 114 passes through the dispersion compensation member 113 and the optical path length correction member 112, is converted from the parallel light beam to the convergent light beam by the collimator 116, and enters the optical fiber 117. The reference light LR that has entered the optical fiber 117 is guided to the polarization controller 118. With the polarization controller 118, the polarization state of the reference light LR is adjusted.

The polarization controller 118 has the same configuration as the polarization controller 103, for example. The reference light LR whose polarization state has been adjusted by the polarization controller 118 is guided to the attenuator 120 through the optical fiber 119, and the light amount thereof is adjusted by the attenuator 120 under the control of the arithmetic and control unit 200. The reference light LR whose light amount has been adjusted by the attenuator 120 is guided to the fiber coupler 122 through the optical fiber 121.

Meanwhile, the measurement light LS generated by the fiber coupler 105 is guided through the optical fiber 127, and is made into the parallel light beam by the collimator lens unit 40. The measurement light LS made into the parallel light beam reaches the dichroic mirror 46 via the optical path length changing unit 41, the optical scanner 42, the OCT focus lens 43, the mirror 44, and the relay lens 45. Then, the measurement light LS is reflected by the dichroic mirror 46, refracted by the objective lens 22, and projected onto the subject's eye E. The measurement light LS is scattered (and reflected) at various depth positions of the subject's eye E. The returning light of the measurement light LS including such backscattered light advances through the same path as the outward path in the opposite direction and is led to the fiber coupler 105, and then reaches the fiber coupler 122 through the optical fiber 128.

The fiber coupler 122 superposes the measurement light LS incident through the optical fiber 128 on the reference light LR incident through the optical fiber 121 to generate interference light. The fiber coupler 122 generates a pair of interference light LC by splitting the interference light generated from the measurement light LS and the reference light LR at a predetermined splitting ratio (for example, 1:1). The pair of the interference light LC emitted from the fiber coupler 122 is guided to the detector 125 through the optical fibers 123 and 124, respectively.

The detector 125 is, for example, a balanced photodiode that includes a pair of photodetectors that respectively detect the pair of the interference light LC, and the balanced photodiode outputs the difference between the pair of detection results obtained by the pair of photodetectors. The detector 125 sends the result of detection (detection signal) to the data acquisition system (DAQ) 130. The clock KC is supplied from the light source unit 101 to the DAQ 130. The clock KC is generated in the light source unit 101 in synchronization with the output timing of each wavelength sweeping (scanning) within a predetermined wavelength range performed by the wavelength tunable type light source. For example, the light source unit 101 optically delays one of the two pieces of branched light obtained by branching the light L0 of each output wavelength, and then generates the clock KC based on the result of the detection of the combined light of the two pieces of branched light. The DAQ 130 performs the sampling of the detection result obtained by the detector 125 based on the clock KC. The DAQ 130 sends the result of the sampling of the detection result obtained by the detector 125 to the arithmetic and control unit 200. For example, the arithmetic and control unit 200 performs Fourier transform etc. on spectral distribution formed based on the detection results obtained by the detector 125 for each series of wavelength scanning (i.e., for each A line). With this, reflection intensity profiles for respective A lines are formed. In addition, the arithmetic and control unit 200 forms image data by applying imaging processing to the reflection intensity profiles for the respective A lines.

[Arithmetic and Control Unit]

The configuration of the arithmetic and control unit 200 will be described. The arithmetic and control unit 200 analyzes the detection signals input from the detector 125 to form an OCT image of the subject's eye E. The arithmetic processing for such image formation is executed in the same manner as the conventional swept source OCT.

In addition, the arithmetic and control unit 200 controls each part of the fundus camera unit 2, the display device 3, and the OCT unit 100. For example, the arithmetic and control unit 200 controls the display device 3 to display the OCT image of the subject's eye E.

Like conventional computers, the arithmetic and control unit 200 includes a microprocessor, a random access memory (RAM), a read only memory (ROM), a hard disk drive, a communication interface, and the like. A storage device such as the hard disk drive stores a computer program for controlling the ophthalmologic imaging apparatus 1. The arithmetic and control unit 200 may include various kinds of circuitry such as a circuit board for forming OCT images. In addition, the arithmetic and control unit 200 may include an operation device (input device) such as a keyboard and a mouse, and a display device such as an LCD.

[Control System]

Figure 3:
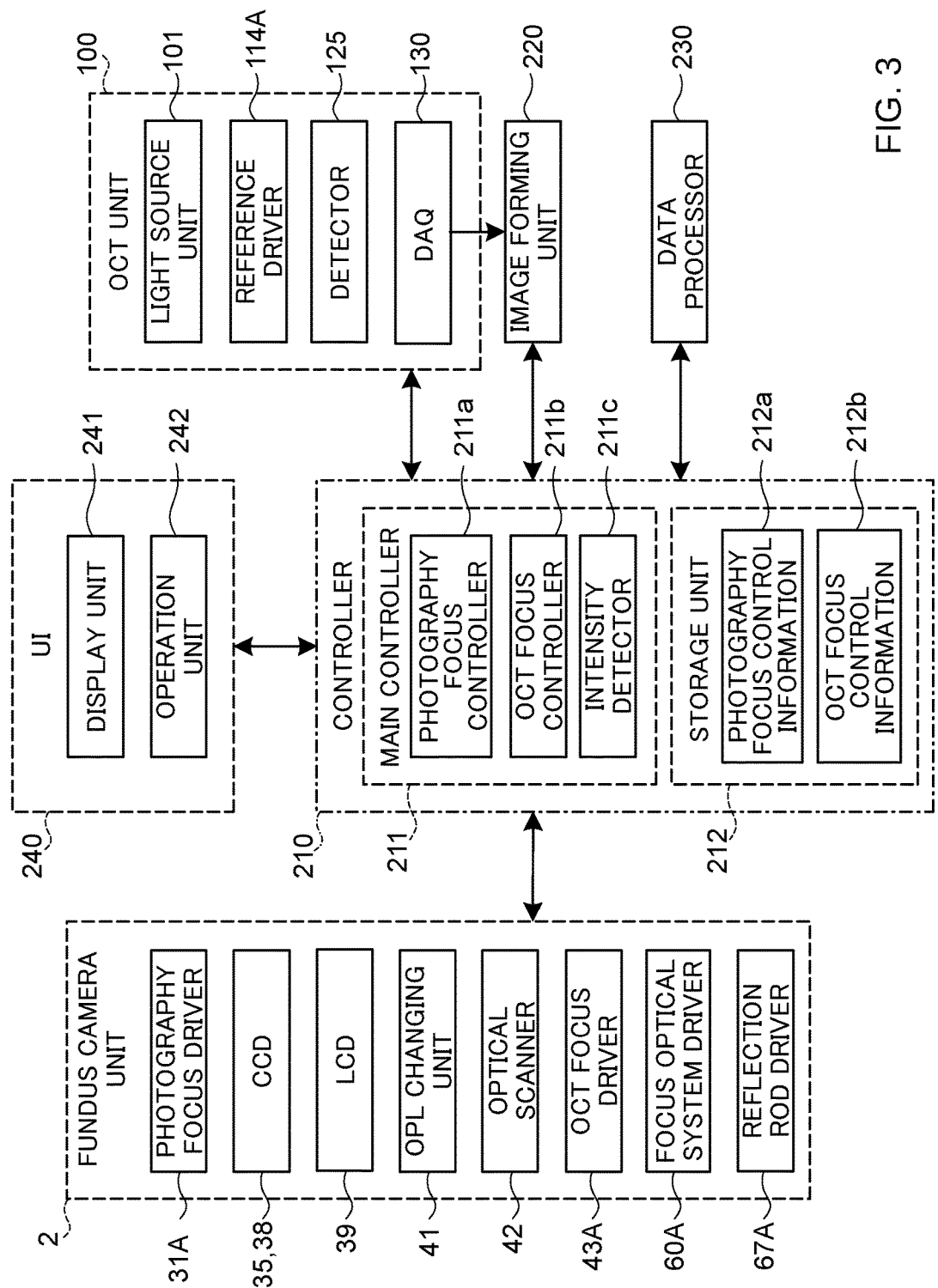
FIG. 3 is a schematic diagram illustrating an example of a configuration of a control system of the ophthalmologic imaging apparatus according to the embodiment.

The configuration of the control system of the ophthalmologic imaging apparatus 1 will be described with reference to FIG. 3. In FIG. 3, some components of the ophthalmologic imaging apparatus 1 are omitted, and the components particularly necessary for describing the present embodiment are selectively shown.

(Controller)

The controller 210 is the center of the control system of the ophthalmologic imaging apparatus 1. The controller 210 includes, for example, a microprocessor, a RAM, a ROM, a hard disk drive, a communication interface, and the like. The controller 210 is provided with the main controller 211 and the storage unit 212.

(Main Controller)

The main controller 211 executes various kinds of controls described above. In particular, as shown in FIG. 3, the main controller 211 controls the photography focus driver 31A, the CCD image sensors 35 and 38, the LCD 39, the optical path length changing unit 41, and the optical scanner 42 of the fundus camera unit 2. In addition, the main controller 211 controls the OCT focus driver 43A, the focus optical system driver 60A, the reflection rod driver 67A, and the like. Further, the main controller 211 controls components of the OCT unit 100 such as the light source unit 101, the reference driver 114A, the detector 125, and the DAQ 130.

The photography focus driver 31A moves the photography focus lens 31 along the optical axis of the photographing optical path. As a result, the focus position of the photographing optical system 30 is changed. Incidentally, the main controller 211 may be configured to control an optical system driver (not illustrated) to move the optical system of the fundus camera unit 2 in the three dimensional manner. This control is used for alignment and tracking. Here, tracking is an operation of moving the optical system of the ophthalmologic imaging apparatus 1 in accordance with the movement of the subject's eye E. To perform tracking, alignment and focusing are performed in advance. Tracking is a function for maintaining a suitable positional relationship in which alignment and focusing are matched, which is realized by moving the optical system of the apparatus in real time according to the position and orientation of the subject's eye E based on the moving image obtained by performing movie shoot of the subject's eye E.

The OCT focus driver 43A moves the OCT focus lens 43 along the optical axis of the measurement optical path. As a result, the focus position of the measurement light LS is changed. The focus position of the measurement light LS corresponds to the depth position (z position) of the beam waist of the measurement light LS.

The focus optical system driver 60A moves the focus optical system 60 along the optical axis of the illumination optical path. The focus optical system driver 60A moves the focus optical system 60 in synchronization with the movement of the photography focus lens 31 induced by the photography focus driver 31A.

The reflection rod driver 67A disposes the reflection rod 67 in the illumination optical path and removes the reflection rod 67 from the illumination optical path. By disposing the reflection rod 67 in the illumination optical path, two split indicator images are displayed on the display device 3. The focus adjustment of the photographing optical system 30 can be performed by analyzing the positions of the two split indicator images as described above.

The reference driver 114A moves the corner cube 114 provided in the reference optical path. As a result, the length of the reference optical path is changed. As described above, a configuration that includes only one of the optical path length changing unit 41 and the combination of the corner cube 114 and the reference driver 114A may be employed.

The main controller 211 includes the photography focus controller 211a, the OCT focus controller 211b, and the intensity detector 211c.

(Photography Focus Controller)

The photography focus controller 211a controls the photography focus driver 31A so as to bring the photographing optical system 30 into focus. Since the operation of the photography focus driver 31A and that of the focus optical system driver 60A are in synchronization with each other, the control for the photography focus driver 31A can be regarded as identical as the control for the focus optical system driver 60A. The photography focus controller 211a executes mutually different focus controls for the photography focus driver 31A between the removed state and the inserted state. In the removed state, the diopter correction lenses 70 and 71 are removed from the photographing optical path. In the inserted state, the diopter correction lens 70 or the diopter correction lens 71 is disposed in the photographing optical path.

<Removed State>

In the removed state, the photography focus controller 211a determines the position of the photography focus lens 31 by controlling the focus optical system driver 60A so that the positional relationship between the two split indicator images is in reference positional relationship. The two split indicator images are acquired by the CCD 35 on the basis of the light returning from the subject's eye E onto which the two split indicators are projected by the focus optical system 60. The photography focus controller 211a analyzes the images acquired by the CCD 35 and controls the photography focus driver 31A so that the positions of the two split indicator images, which are arranged in the vertical direction, depicted in the image match. The photography focus controller 211a determines the position of the photography focus lens 31 in the photographing optical path to be the focus position when the two split indicator images arranged in the vertical direction match. The photography focus controller 211a controls the photography focus driver 31A to move the photography focus lens 31 to the position determined. The photography focus controller 211a can determine the position of the photography focus lens 31 by referring to the photography focus control information 212a (described later) prestored in the storage unit 212 corresponding to the position of the focus optical system 60 where the two split indicator images arranged in the vertical direction match.

<Inserted State>

As described above, a split indicator image cannot be acquired by the photographing optical system 30 in the inserted state. In the inserted state, the photography focus controller 211a determines the position of the photography focus lens 31 based on the position of the OCT focus lens 43 determined by the OCT focus controller 211b described later. As will be described later, the OCT focus controller 211b determines the position of the OCT focus lens 43 based on the interference light LC detected by the interference optical system. Therefore, the photography focus controller 211a can determine the position of the photography focus lens 31 based on the interference light LC. The photography focus controller 211a can determine the position of the photography focus lens 31 in such a way that the intensity of the interference light LC detected by the intensity detector 211c described later is maximized. Further, the photography focus controller 211a may determine the position of the photography focus lens 31 based on the control content (control history) for the OCT focus driver 43A by the OCT focus controller 211b. The photography focus controller 211a controls the photography focus driver 31A to move the photography focus lens 31 to the position determined. The photography focus controller 211a can determine the position of the photography focus lens 31 by referring to the OCT focus control information 212b (described later) stored in the storage unit 212 in advance.

(OCT Focus Controller)

The OCT focus controller 211b controls the OCT focus driver 43A to bring the interference optical system into focus. As described above, the OCT focus controller 211b determines the position of the OCT focus lens 43 based on the interference light LC detected by the interference optical system. As a specific example thereof, the OCT focus controller 211b determines the position of the OCT focus lens 43 so that the intensity of the interference light LC detected by the intensity detector 211c is maximized. The OCT focus controller 211b controls the OCT focus driver 43A to move the OCT focus lens 43 to the focus position determined.

(Intensity Detector)

The intensity detector 211c detects the intensity of the interference light detected by the interference optical system. The intensity detector 211c detects the intensity of the interference light based on the detection signal detected by the detector 125. The intensity detector 211c can detect the maximum value of the intensity of the interference light. The OCT focus controller 211b determines the focus position of the OCT focus lens 43 so that the intensity of the interference light detected by the intensity detector 211c in a scan area or at a scan position(s) of the subject's eye E set in advance is maximized.

(Storage Unit)

The storage unit 212 stores various kinds of data. Examples of the data stored in the storage unit 212 include image data of an OCT image, image data of a fundus image, and subject's eye information. The subject's eye information includes information related to a subject such as patient ID and name, information related to a subject's eye such as identification information of left eye/right eye, and the like. In addition, the storage unit 212 stores various kinds of programs and various kinds of data to run the ophthalmologic imaging apparatus 1.

The storage unit 212 stores the photography focus control information 212a and the OCT focus control information 212b in advance.

As shown in FIG. 4, the photography focus control information 212a is control information in which the positions F1, F2, . . . of the focus optical system 60, at which the positional relationship between the two split indicator images corresponds to the aforementioned reference positional relationship, are associated with the positions D1, D2, . . . of the photography focus lens 31. According to the diopter of the subject's eye E, the position of the focus optical system 60 at which the positional relationship between the two split indicator images becomes the reference positional relationship on the illumination optical path is determined. In addition, according to the diopter of the subject's eye E, the position of the photography focus lens 31 on the photographing optical path, in which the photographing optical system 30 is brought into focus, is determined. Therefore, the diopter of the subject's eye E can be determined from the position of the focus optical system 60 and the position of the photography focus lens 31 can be determined from the determined diopter of the subject's eye E. Thus, the photography focus control information 212a shown in FIG. 4 can be generated in advance. The photography focus controller 211a specifies the position of the photography focus lens 31 from the position of the focus optical system 60 based on the photography focus control information 212a. At this time, the photography focus controller 211a can execute interpolation processing using the control information stored in advance as the photography focus control information 212a and specify the focus position of the photography focus lens 31 based on the new control information obtained by the interpolation processing.

As shown in FIG. 5, the OCT focus control information 212b is control information in which the positions C1, C2, . . . of the OCT focus lens 43 are associated with the positions d1, d2, . . . of the photography focus lens 31. According to the diopter of the subject's eye E, the position of the OCT focus lens 43 in the measurement optical path, in which the interference optical system is brought into focus, is determined. In addition, as described above, the position of the photography focus lens 31 in the photographing optical path, in which the photographing optical system 30 is brought into focus, is determined according to the diopter of the subject's eye E. Therefore, the diopter of the subject's eye E can be obtained from the position of the OCT focus lens 43 and the position of the photography focus lens 31 can be obtained from the obtained diopter of the subject's eye E. Thus, the OCT focus control information 212b shown in FIG. 5 can be generated in advance. The photography focus controller 211a specifies the position of the photography focus lens 31 from the position of the OCT focus lens 43 based on the OCT focus control information 212b. At this time, the photography focus controller 211a can execute interpolation processing using the control information stored in advance as the OCT focus control information 212b and specify the focus position of the photography focus lens 31 based on the new control information obtained by the interpolation processing.

(Image Forming Unit)

The image forming unit 220 forms image data of a cross sectional image of the fundus Ef based on detection signals from the detector 125 (DAQ 130). That is, the image forming unit 220 forms the image data of the subject's eye E based on detection results of the interference light LC obtained by the interference optical system. As with the conventional swept source OCT, the image formation process includes noise removal (noise reduction), filtering, fast Fourier transform (FFT), and the like. The image data acquired in this manner is a data set including a group of image data formed by imaging the reflection intensity profiles for a plurality of A lines. Here, the plurality of A lines corresponds to the paths of the respective pieces of the measurement light LS in the eye E.

In order to improve the image quality, it is possible to repeatedly perform scan with the same pattern a plurality of times to collect a plurality of data sets, and to compose the plurality of data sets (to perform addition and average).

Further, the image forming unit 220 forms an image in which two or more split indicator images are depicted from the image signal detected by the CCD 35 based on the returning light of two or more split indicators from the eye E that has passed through the photography focus lens 31. Note that the main controller 211 may be configured to execute the formation of the image in which the two or more split indicator images are depicted.

The image forming unit 220 includes, for example, the circuitry described above. Note that "image data" and an "image" based on the image data may not be distinguished from each other in the present specification. In addition, a site of the subject's eye E and an image of the site may not be distinguished from each other.

(Data Processor)

The data processor 230 performs various kinds of data processing (e.g., image processing) and various kinds of analysis on an image formed by the image forming unit 220. For example, the data processor 230 performs various correction processes such as brightness correction and dispersion correction of images. The data processor 230 performs various kinds of image processing and various kinds of analysis on images captured by the fundus camera unit 2 (e.g., fundus images, anterior segment images, etc.).

The data processor 230 can form volume data (voxel data) of the subject's eye E by executing known image processing such as interpolation processing that interpolates pixels between cross sectional images. In the case of displaying an image based on the volume data, the data processor 230 executes a rendering process on the volume data so as to form a pseudo three dimensional image viewed from a specific line-of-sight direction.

The data processor 230 can execute registration (position matching) between a fundus image and an OCT image. When a fundus image and an OCT image are acquired in parallel, the registration between the fundus image and the OCT image, which have been (almost) simultaneously obtained, can be performed using the optical axis of the photographing optical system 30 as a reference. Regardless of the acquisition timing of a fundus image and that of an OCT image, registration between a fundus image and an OCT image can be achieved by executing registration between the fundus image and a front image formed by projecting at least part of the image area in the OCT image corresponding to the fundus Ef onto the xy plane. Such a registration technique can also be employed when the optical system for acquiring fundus images and the optical system for OCT are not coaxial with each other. Further, even when the optical system for acquiring fundus images and the optical system for OCT are not coaxial with each other, if the relative positional relationship between these optical systems is known, registration can be performed with referring to the relative positional relationship in a similar manner to the case in which the optical systems are coaxial with each other.

The data processor 230 that functions as above includes, for example, a microprocessor, a RAM, a ROM, a hard disk drive, a circuit board, and the like. The storage device such as the hard disk drive stores, in advance, a computer program for causing the microprocessor to execute the functions described above.

(User Interface)

The user interface 240 includes the display unit 241 and the operation unit 242. The display unit 241 includes the display device of the arithmetic and control unit 200 and the display device 3 as described above. The operation unit 242 includes the operation device of the arithmetic and control unit 200 as described above. The operation unit 242 may include various kinds of buttons and keys provided on the housing of the ophthalmologic imaging apparatus 1, or provided outside the ophthalmologic imaging apparatus 1. Further, the display unit 241 may include various kinds of display devices, such as a touch panel placed on the housing of the fundus camera unit 2.

Note that the display unit 241 and the operation unit 242 need not necessarily be formed as separate devices. For example, a device like a touch panel, which has a display function integrated with an operation function, can be used. In such a case, the operation unit 242 includes the touch panel and a computer program. The content of an operation performed using the operation unit 242 is fed to the controller 210 as an electrical signal. Moreover, operations and inputs of information may be performed using a graphical user interface (GUI) displayed on the display unit 241 and the operation unit 242.

The photographing optical system 30 is an example of the "first optical system" according to the embodiment. The photographing optical path which is the optical path of the photographing optical system 30 is an example of the "first optical path" according to the embodiment. The photography focus lens 31 is an example of the "first focus lens" according to the embodiment. The CCD 35 is an example of the "first light receiving element" according to the embodiment. The photography focus driver 31A is an example of the "first driver" according to the embodiment. The photography focus controller 211a is an example of the "first focus controller" according to the embodiment.

The combination of the OCT unit 100, the collimator lens unit 40, the optical path length changing unit 41, the optical scanner 42, the OCT focus lens 43, the mirror 44 and the relay lens 45 is an example of the "second optical system" or an example of the "interference optical system" according to the embodiment. The measurement optical path, which is the optical path of the measurement light LS and the optical path of the returning light of the measurement light, is an example of the "second optical path" according to the embodiment. The OCT focus lens 43 is an example of the "second focus lens" according to the embodiment. The detector 125 is an example of the "second light receiving element" according to the embodiment. The OCT focus driver 43A is an example of the "second driver" according to the embodiment. The OCT focus controller 211b is an example of the "second focus controller" according to the embodiment.

The illumination optical path, which is the optical path of the illumination optical system 10, is an example of the "third optical path" according to the embodiment. The focus optical system 60 is an example of the "focus indicator projection optical system" according to the embodiment. The pair of split indicators is an example of the "focus indicator" according to the embodiment. The focus optical system driver 60A is an example of the "third driver" according to the embodiment. The photography focus control information 212a is an example of the "second control information" according to the embodiment. The OCT focus control information 212b is an example of the "first control information" according to the embodiment.

Operation Example

The operation of the ophthalmologic imaging apparatus 1 will be described. The ophthalmologic imaging apparatus 1 according to the embodiment performs acquisition of an image of the fundus Ef of the subject's eye E using the fundus camera unit 2 and acquisition of a cross sectional image of the fundus Ef using the OCT unit 100 etc. The operation of the OCT unit 100 etc. of the ophthalmologic imaging apparatus 1 for acquiring a cross sectional image of the fundus Ef is known. In the following, an operation example when the fundus camera unit 2 acquires an image of the fundus Ef of the subject's eye E will be described.

Before describing the operation example of the ophthalmologic imaging apparatus 1 according to the embodiment, an operation example of an ophthalmologic imaging apparatus according to a comparative example will be described.

Figure 6:
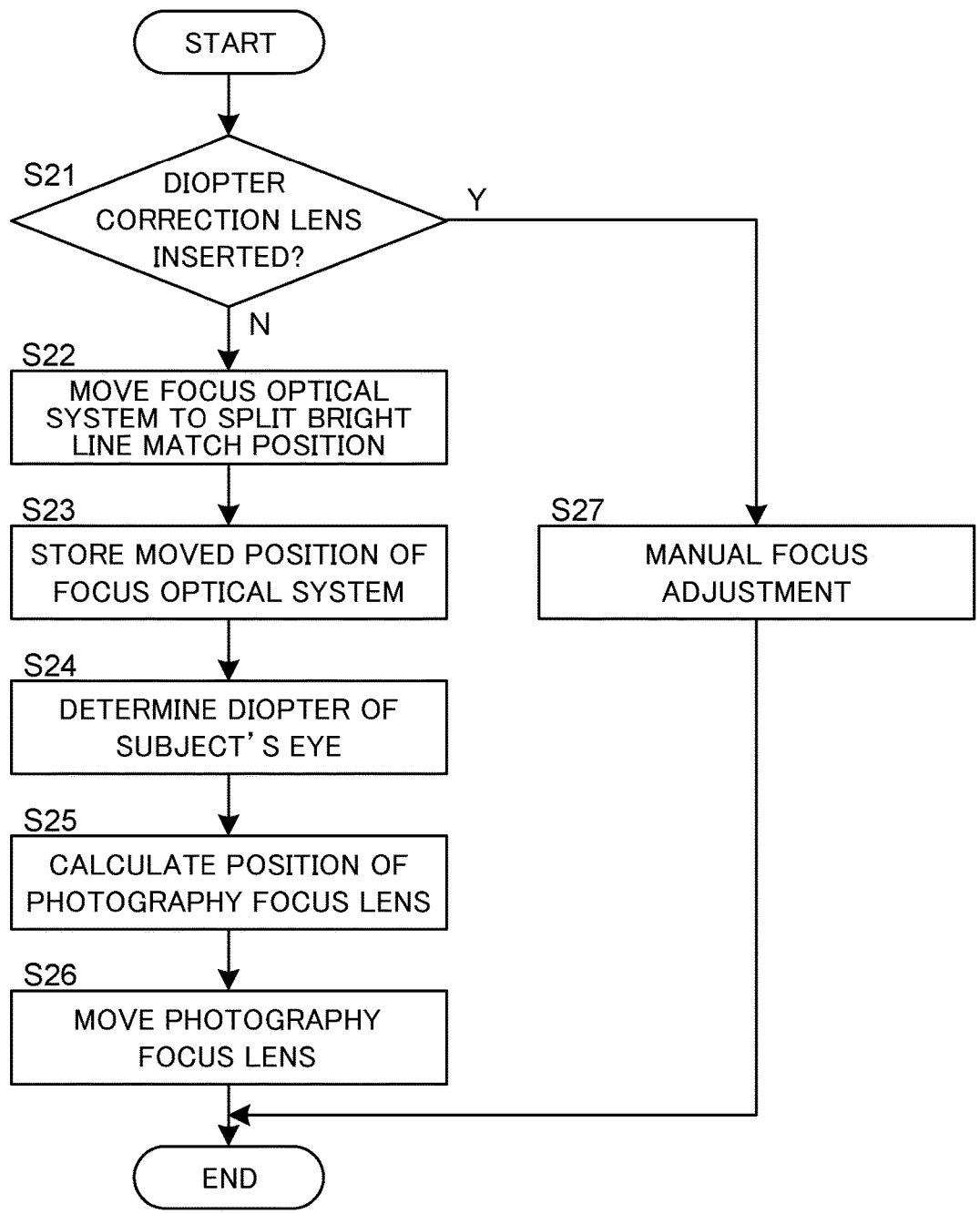
FIG. 6 is a flow chart of an operation example of an ophthalmologic imaging apparatus according to a comparative example of the embodiment.

FIG. 6 shows a flow chart of an operation example of the ophthalmologic imaging apparatus according to the comparative example. In this operation example, it is assumed that alignment (auto alignment) for photographing has already been performed and tracking has already been started.

(S21)

When the diopter correction lens has been inserted into the photographing optical path (S21: Y), the operation of the ophthalmologic imaging apparatus according to the comparative example proceeds to S27. When the diopter correction lens has been removed from the photographing optical path (S21: N), the operation of the ophthalmologic imaging apparatus according to the comparative example proceeds to S22.

(S22)

When the diopter correction lens has been removed from the photographing optical path (S21: N), the controller, which controls the ophthalmologic imaging apparatus according to the comparative example, controls the reflecting rod to be inserted into the illumination optical path, and controls the focus optical system to be moved up to a position where the split indicator images arranged in the vertical direction match (up to a match position of the split bright lines).

(S23)

When the focus optical system has been moved up to the position where the split indicator images arranged in the vertical direction match, the controller stores the moved position of the focus optical system after the movement in the storage unit.

(S24)

The storage unit stores, in advance, the control information in which moved positions of the focus optical system are associated with diopters of the subject's eye E. By referring to the control information stored in the storage unit, the controller determines the diopter of the subject's eye E from the moved position of the focus optical system stored in S23.

(S25)

The diopter of the subject's eye E is associated in advance with the position of the photography focus lens for changing the focus position of the photographing optical system. The controller calculates the position of the photography focus lens from the diopter of the subject's eye E determined in S24.

(S26)

The controller moves the photography focus lens to the position calculated in S25. After the photography focus lens has been moved to the focus position, the ophthalmologic imaging apparatus according to the comparative example performs photographing of the fundus Ef. This terminates the operation of the ophthalmologic imaging apparatus according to the comparative example (END).

(S27)

When the diopter correction lens has been inserted into the photographing optical path (S21: Y), the ophthalmologic imaging apparatus according to the comparative example receives a user's operation performed on the operation unit (not shown) and manual focus adjustment is performed. That is, the photography focus lens is manually moved. After the position of the photography focus lens has been manually adjusted, the ophthalmologic imaging apparatus according to the comparative example performs photographing of the fundus Ef. This terminates the operation of the ophthalmologic imaging apparatus according to the comparative example (END).

As described above, with the ophthalmologic imaging apparatus according to the comparative example, the focus control using the split indicator images described above becomes impossible when the diopter correction lens has been inserted into the photographing optical path, and therefore, manual focus adjustment is necessary to be performed.

Figure 7:
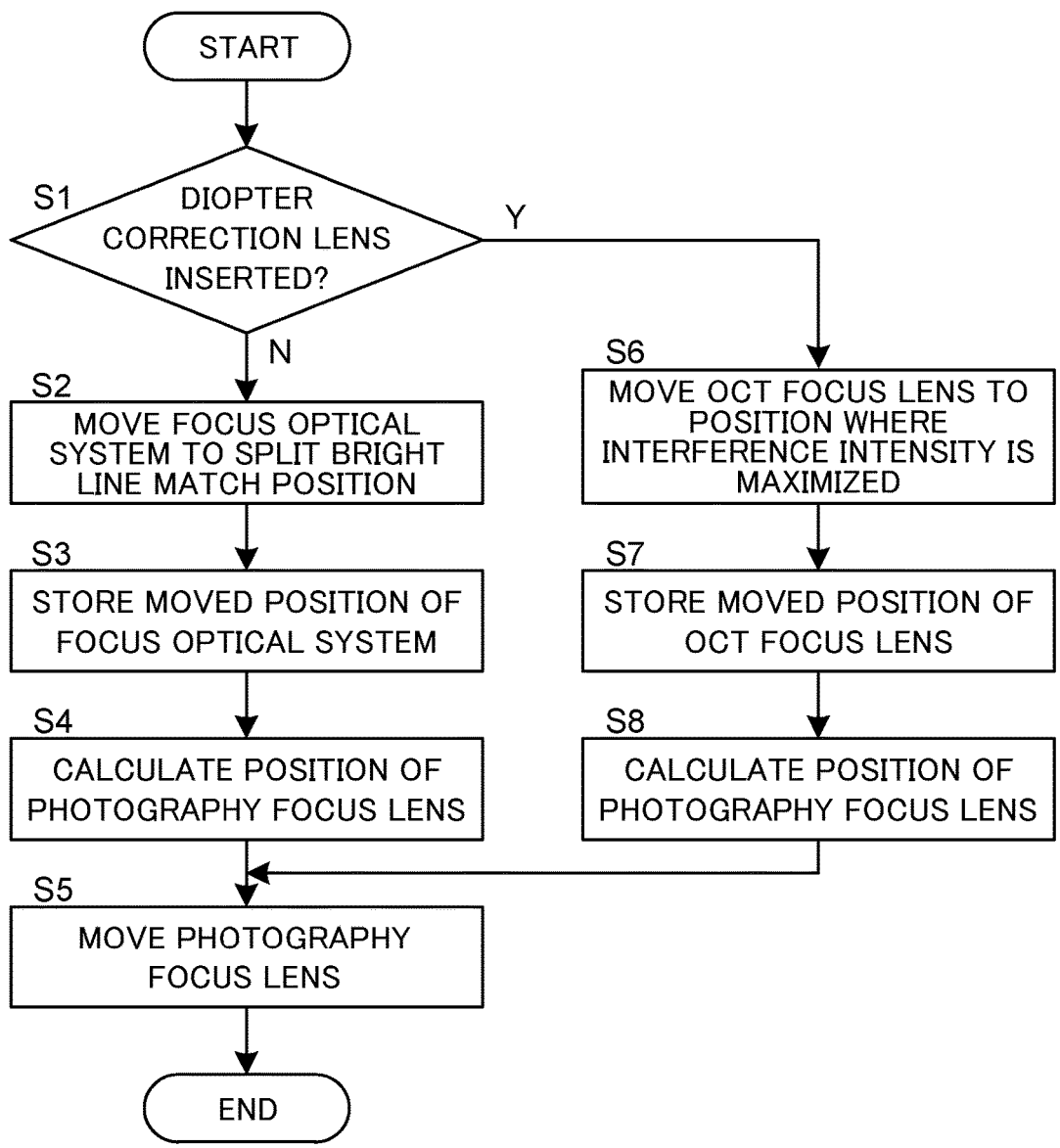
FIG. 7 is a flow chart of an operation example of the ophthalmologic imaging apparatus according to the embodiment.

FIG. 7 shows a flow chart of an operation example of the ophthalmologic imaging apparatus 1 according to the embodiment. In this operation example, it is assumed that alignment (auto alignment) for photographing has already been performed and tracking has already been started.

(S1)

First, the main controller 211 determines whether or not the diopter correction lens 70 or 71 is inserted in the photographing optical path. The main controller 211 can determine whether or not the diopter correction lens 70 or 71 is inserted in the photographing optical path based on the state of an operation knob (the operation unit 242) used for inserting and removing the diopter correction lens 70 or the diopter correction lens 71 into and from the photographing optical path. In addition, the main controller 211 can determine whether or not the diopter correction lens 70 or 71 is inserted in the photographing optical path based on a detection result obtained by a sensor provided in the moving mechanism that moves the diopter correction lenses 70 and 71. When the main controller 211 has determined that the diopter correction lens 70 or the diopter correction lens 71 has been inserted into the photographing optical path (S1: Y), the operation of the ophthalmologic imaging apparatus 1 proceeds to S7. When the main controller 211 has determined that the diopter correction lens 70 and the diopter correction lens 71 have been removed from the photographing optical path (S1: N), the operation of the ophthalmologic imaging apparatus 1 moves to S2.

(S2)

When the main controller 211 has determined that the diopter correction lens 70 and the diopter correction lens 71 have been removed from the photographing optical path (S1: N), the photography focus controller 211a executes control of the reflection rod driver 67A to insert the reflection rod 67 into the illumination optical path. Subsequently, the photography focus controller 211a executes control of the focus optical system driver 60A to move the focus optical system 60 up to the position where the split indicator images arranged in the vertical direction match (up to the match position of the split bright lines).

(S3)

When the focus optical system 60 has been moved to the position where the split indicator images arranged in the vertical direction match, the main controller 211 (the photography focus controller 211a) stores the moved position of the focus optical system 60 in the storage unit 212.

(S4)

By referring to the photography focus control information 212a stored in the storage unit 212, the photography focus controller 211a calculates the position of the photography focus lens 31 from the moved position of the focus optical system 60 stored in S3.

(S5)

The photography focus controller 211a controls the photography focus driver 31A to move the photography focus lens 31 to the position calculated in S4. After the photography focus lens 31 has been moved to the focus position, the ophthalmologic imaging apparatus 1 performs photographing of the fundus Ef. This terminates the operation of the ophthalmologic imaging apparatus 1 according to the embodiment (END).

(S6)

When the main controller 211 has determined that the diopter correction lens 70 or the diopter correction lens 71 has been inserted into the photographing optical path (S1: Y), the OCT focus controller 211b controls the ophthalmologic imaging apparatus 1 to perform OCT measurement and controls the intensity detector 211c to start detection of the interference light LC. The OCT focus controller 211b controls the OCT focus driver 43A to move the OCT focus lens 43 up to the position where the intensity of the interference light LC detected by the intensity detector 211c is maximized.

(S7)

When the OCT focus lens 43 has been moved to the position where the intensity of the interference light LC is maximized, the main controller 211 (the OCT focus controller 211b) stores the moved position of the OCT focus lens 43 after the movement in the storage unit 212.

(S8)

By referring to the OCT focus control information 212b stored in the storage unit 212, the photography focus controller 211a calculates the position of the photography focus lens 31 from the moved position of the OCT focus lens 43 stored in S8. Thereafter, the operation of the ophthalmologic imaging apparatus 1 proceeds to S5.

As described above, when the diopter correction lens has been inserted into the photographing optical path, it is necessary to manually adjust the focus in the comparative example. On the other hand, the ophthalmologic imaging apparatus 1 according to the embodiment is capable of performing automatic focusing.

Note that the present embodiment has described the case where the "second optical system" according to the embodiment is an optical system that uses OCT to image the subject's eye E. However, the "second optical system" according to the embodiment may be an observation system that guides light from the subject's eye E to an eyepiece.

[Effects]

The effects of the ophthalmologic imaging apparatus according to the embodiment will be described.

An ophthalmologic imaging apparatus of an embodiment (e.g., the ophthalmologic imaging apparatus 1) includes a first optical system (e.g., the photographing optical system 30), a first driver (e.g., the photography focus driver 31A), a first focus controller (e.g., the photography focus controller 211a). The first optical system includes a first focus lens (e.g., the photography focus lens 31) and a diopter correction lens (e.g., the diopter correction lens 70 or 71) and is configured to guide light from a subject's eye (e.g., the subject's eye E) to a first light receiving element (e.g., the CCD 35). The first focus lens is movable along an optical axis of a first optical path (e.g., the photographing optical path). The diopter correction lens is insertable into and removable from the first optical path. The first driver is configured to move the first focus lens. The first focus controller is configured to execute mutually different focus control processes of the first driver in a removed state in which the diopter correction lens has been removed from the first optical path and in an inserted state in which the diopter correction lens has been inserted into the first optical path.

According to such a configuration, in the inserted state, focus control different from focus control executed in the removed state is executed. Therefore, automatic focus adjustment can be performed even in the case where the optical relationship changes due to the insertion of the diopter correction lens. More specifically, the first optical system can be brought into focus with the so-called auto-focus function in a state where the diopter correction lens has been inserted into the first optical path, as well as in a state where the diopter correction lens has been removed from the first optical path.

In addition, the ophthalmologic imaging apparatus according to the embodiment may include a second optical system (e.g., the interference optical system includes the OCT unit 100, the collimator lens unit 40, the optical path length changing unit 41, the optical scanner 42, the OCT focus lens 43, the mirror 44 and the relay lens 45, etc.), a second driver (e.g., the OCT focus driver 43A), and a second focus controller (e.g., the OCT focus controller 211b). The second optical system includes a second focus lens (e.g., the OCT focus lens 43), and is configured to guide the light from the subject's eye to a second light receiving element (e.g., the detector 125) or an eyepiece. The second focus lens is movable along an optical axis of a second optical path (e.g., the optical path of the measurement light or the optical path of the returning light of the measurement light). The second driver is configured to move the second focus lens. The second focus controller is configured to determine a position of the second focus lens by executing focus control of the second driver and to move the second focus lens to the focus position determined. The first focus controller determines a position of the first focus lens based on the position of the second focus lens determined by the second focus controller and moves the first focus lens to the focus position determined in the inserted state.

According to such a configuration, the contents of the focus control for the second driver is reflected in the focus control for the first driver in the inserted state. Therefore, it is possible to automatically execute high-precision focus control not only in the removed state but also in the inserted state.

Further, in the ophthalmologic imaging apparatus according to the embodiment, the second optical system includes an interference optical system. The interference optical system splits light (e.g., the light L0) from a light source (e.g., the light source unit 101) into measurement light (e.g., the measurement light LS) and reference light (e.g., the reference light LR), projects the measurement light onto the subject's eye, and detects interference light (e.g., the interference light LC) generated from returning light of the measurement light from the subject's eye and the reference light by the second light receiving element. The second focus lens is disposed in an optical path of the measurement light and the returning light. The second focus controller determines the position of the second focus lens based on the interference light detected by the interference optical system.

According to such a configuration, the first optical system can be brought into focus on the basis of the interference light generated by the interference optical system. Therefore, it becomes possible to automatically execute high-precision focus control in the inserted state in the similar manner as in the removed state.

Further, the ophthalmologic imaging apparatus according to the embodiment includes an intensity detector (e.g., the intensity detector 211c). The intensity detector is configured to detect intensity of the interference light detected by the interference optical system. The second focus controller determines the position of the second focus lens so that the intensity of the interference light detected by the intensity detector is maximized.

According to such a configuration, the first optical system can be brought into focus on the basis of the intensity of the interference light. Therefore, it becomes possible to automatically execute high-precision focus control with a simple control process in the inserted state.

Further, the ophthalmologic imaging apparatus according to the embodiment includes a storage unit (e.g., the storage unit 212). The storage unit is configured to store, in advance, first control information (e.g., the OCT focus control information 212b) in which positions of the second focus lens are associated with positions of the first focus lens. The first focus controller determines the position of the first focus lens based on the position of the second focus lens determined by the second focus controller and the first control information in the inserted state.

According to such a configuration, the first optical system can be brought into focus on the basis of the first control information. Therefore, it is possible to simplify the focus control and increase the speed of the focus control in the inserted state.

Further, the ophthalmologic imaging apparatus according to the embodiment includes an illumination optical system (e.g., the illumination optical system 10), a focus indicator projection optical system (e.g., the focus optical system 60), and a third driver (e.g., the focus optical system driver 60A). The illumination optical system is configured to project an illumination light beam onto the subject's eye via a third optical path (e.g., the illumination optical path) coupled with the first optical path at a location between the subject's eye and the diopter correction lens. The focus indicator projection optical system is configured to project a focus indicator (e.g., the split indicator) onto the subject's eye via the third optical path. The third driver is configured to move the focus indicator projection optical system along an optical axis of the third optical path. The first light receiving element receives returning light of the focus indicator from the subject's eye which has passed through the first focus lens. The first focus controller determines the position of the first focus lens by controlling the third driver based on the position of an image of the focus indicator acquired by the first light receiving element and moves the first focus lens to the focus position determined in the removed state.

According to such a configuration, in addition to the aforementioned effects, it becomes possible to automatically execute high-precision focus control based on the position of the image of the focus indicator acquired by the focus optical system in the removed state.

First Modification Example

The photography focus controller 211a according to the embodiment is not limited to one that obtains the focus position of the photography focus lens 31 based on the OCT focus control information 212b shown in FIG. 5.

The configuration and operation of the ophthalmologic imaging apparatus according to the first modification example are almost the same as those of the ophthalmologic imaging apparatus 1 according to the embodiment. Hereinafter, the ophthalmologic imaging apparatus according to the first modification example will be described focusing on differences from the present embodiment.

Figure 8:
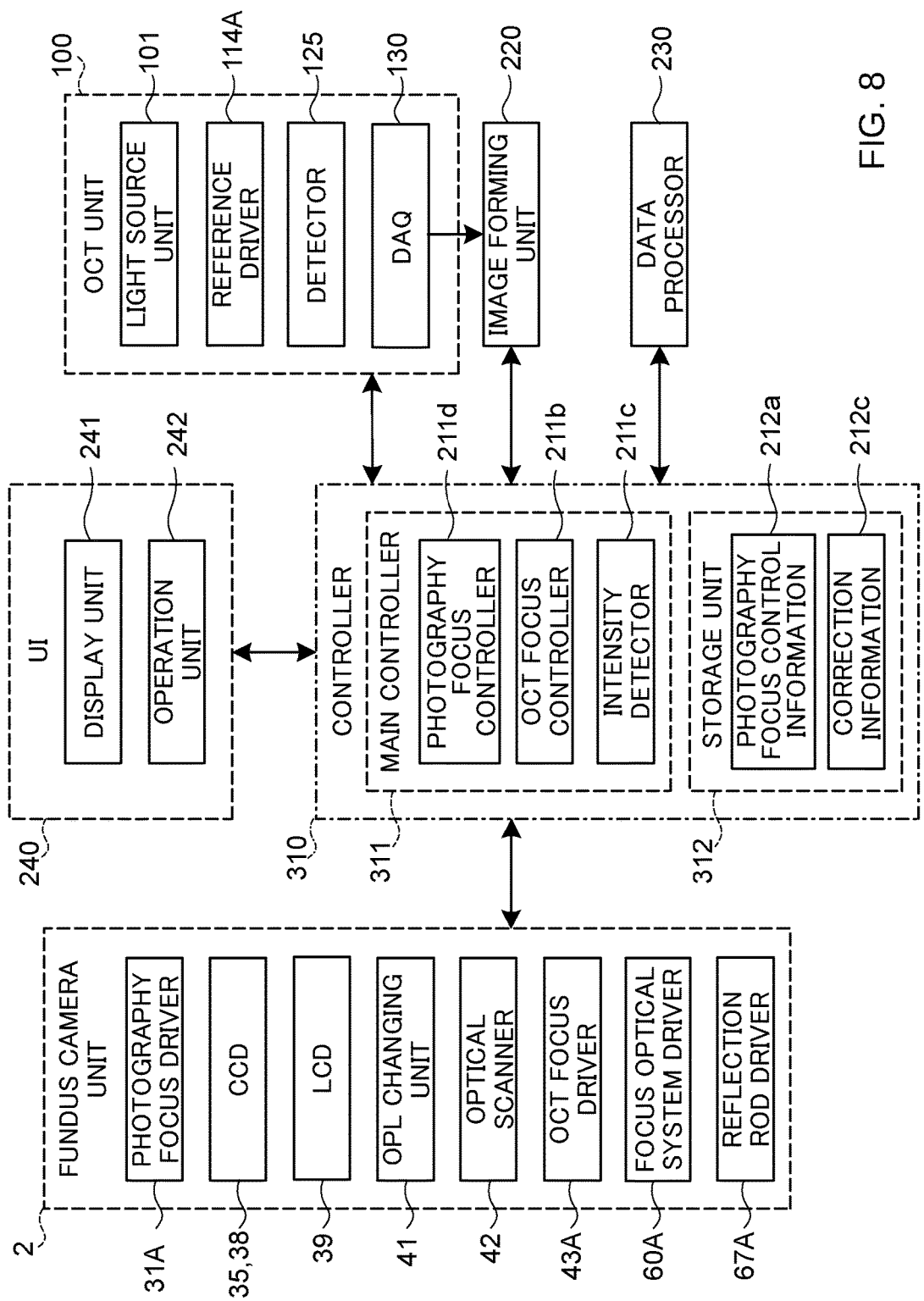
FIG. 8 is a schematic diagram illustrating an example of a configuration of a control system of an ophthalmologic imaging apparatus according to the first modification example of the embodiment.

FIG. 8 shows an example of a block diagram of the control system of the ophthalmologic imaging apparatus according to the first modification example. In FIG. 8, parts similar to those in FIG. 3 are denoted by the same reference symbols, and description thereof is omitted as appropriate. The main difference between the configuration of the control system of the ophthalmologic imaging apparatus according to the first modification example and the configuration of the control system of the ophthalmologic imaging apparatus 1 according to the embodiment is that the correction information 212c is stored in the storage unit 312 instead of the OCT focus control information 212b.

In the ophthalmologic imaging apparatus according to the first modification example, the controller 310 is provided in place of the controller 210. The controller 310 includes the main controller 311 and the storage unit 312. The main controller 311 includes the photography focus controller 211d, the OCT focus controller 211b, and the intensity detector 211c. The storage unit 312 stores the photography focus control information 212a and the correction information 212c.

The correction information 212c is control information for correcting the photography focus control information 212a in order to obtain the position of the photography focus lens 31 from the position of the OCT focus lens 43. The correction information 212c may be, for example, control information in which positions of the OCT focus lens 43 are associated with correction values. The correction information 212c may include correction values corresponding to the respective positions D1, D2, . . . of the photography focus lens 31. The correction information 212c may also be information in which one correction value is assigned to a plurality of positions among the focus positions D1, D2, . . . .

The photography focus controller 211d corrects the position of the photography focus lens obtained from the photography focus control information 212a based on the correction information 212c in a state where the diopter correction lens 70 or the diopter correction lens 71 has been inserted into the photographing optical path. With this, the photography focus controller 211d determines a new position of the photography focus lens 31. The photography focus controller 211d executes control of the photography focus driver 31A and move the photography focus lens 31 to the new focus position determined.

[Effects]

The ophthalmologic imaging apparatus according to the embodiment includes a storage unit (e.g., the storage unit 312). The storage unit is configured to store second control information (e.g., the photography focus control information 212a) and correction information (e.g., the correction information 212c) in advance. The second control information is information in which positions of the focus indicator projection optical system at which the position of the image of the focus indicator matches a predetermined position are associated with positions of the first focus lens. The correction information is information for correcting the second control information. The first focus controller (e.g., the photography focus controller 211d) determines the position of the first focus lens based on the second control information and moves the first focus lens to the focus position determined in the removed state. The first focus controller determines a new position of the first focus lens by correcting the position of the first focus lens stored in the storage unit based on the correction information and moves the first focus lens to the new focus position in the inserted state.

According to such a configuration, the first optical system can be brought into focus on the basis of the second control information in the removed state, while the first optical system can be brought into focus on the basis of the second control information and the correction information in the inserted state. Therefore, it is possible to simplify and increase the speed of the focus control using the diopter correction lens.

Second Modification Example

In the ophthalmologic imaging apparatus 1 according to the embodiment, the case has been described in which mutually different focus control processes are executed in accordance with the determination result as to whether or not the diopter correction lens 70 or 71 has been inserted into the photographing optical path. However, the operation of the ophthalmologic imaging apparatus 1 according to the embodiment is not limited to this.

The configuration and operation of the ophthalmologic imaging apparatus according to the second modification example are almost the same as those of the ophthalmologic imaging apparatus 1 according to the embodiment. Hereinafter, the ophthalmologic imaging apparatus according to the second modification will be described focusing on differences from the present embodiment.

Figure 9:
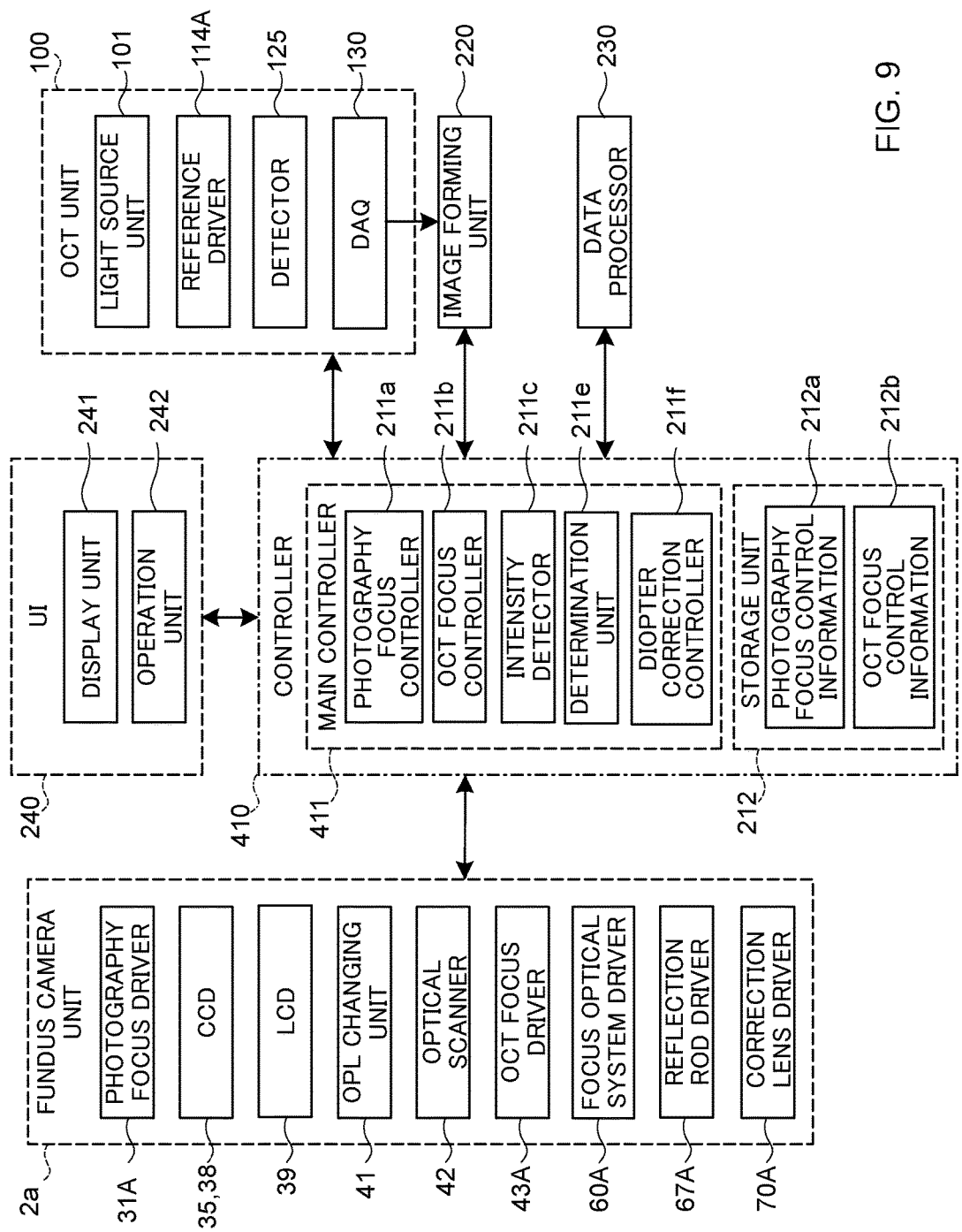
FIG. 9 is a schematic diagram illustrating an example of a configuration of a control system of an ophthalmologic imaging apparatus according to the second modification example of the embodiment.

FIG. 9 shows an example of a block diagram of the control system of the ophthalmologic imaging apparatus according to the second modification example. In FIG. 9, parts similar to those in FIG. 3 are denoted by the same reference symbols, and description thereof is omitted as appropriate. The main difference between the configuration of the control system of the ophthalmologic imaging apparatus according to the second modification example and the configuration of the control system of the ophthalmologic imaging apparatus 1 according to the embodiment is that the fundus camera unit 2a is provided instead of the fundus camera unit 2, and that the controller 410 is provided instead of the controller 210.

The difference between the configuration of the fundus camera unit 2a and that of the fundus camera unit 2 is that the correction lens driver 70A is provided. The correction lens driver 70A moves the diopter correction lenses 70 and 71. The correction lens driver 70A receives the control from the diopter correction controller 211f (described later) and inserts or removes the diopter correction lens 70 or the diopter correction lens 71 into or from the photographing optical path.

The difference between the controller 410 and the controller 210 is that the main controller 411 is provided in place of the main controller 211. The main controller 411 includes the photography focus controller 211a, the OCT focus controller 211b, the intensity detector 211c, the determination unit 211e, and the diopter correction controller 211f.

The photography focus controller 211a controls the photography focus driver 31A within a predetermined focusable range to determine the position of the photography focus lens 31. The determination unit 211e determines whether or not the photographing optical system 30 has been brought into focus by the photography focus lens 31 in the predetermined focusable range in a state where the diopter correction lenses 70 and 71 have been removed from the photographing optical path. For example, the determination unit 211e determines that the photographing optical system 30 has been brought into focus by the photography focus lens 31 when the split indicator images arranged in the vertical direction match within the aforementioned focusable range. In addition, the determination unit 211e determines that the photographing optical system 30 has not been brought into focus by the photography focus lens 31 when the split indicator images arranged in the vertical direction do not match within the aforementioned focusable range, for example.

The diopter correction controller 211f controls the correction lens driver 70A based on the determination result obtained by the determination unit 211e. When the determination unit 211e has determined that the photographing optical system 30 has not become in focus by the photography focus lens 31, the diopter correction controller 211f controls the correction lens diverter 70A to insert the diopter correction lens 70 or the diopter correction lens 71 into the photographing optical path.

Figure 10:
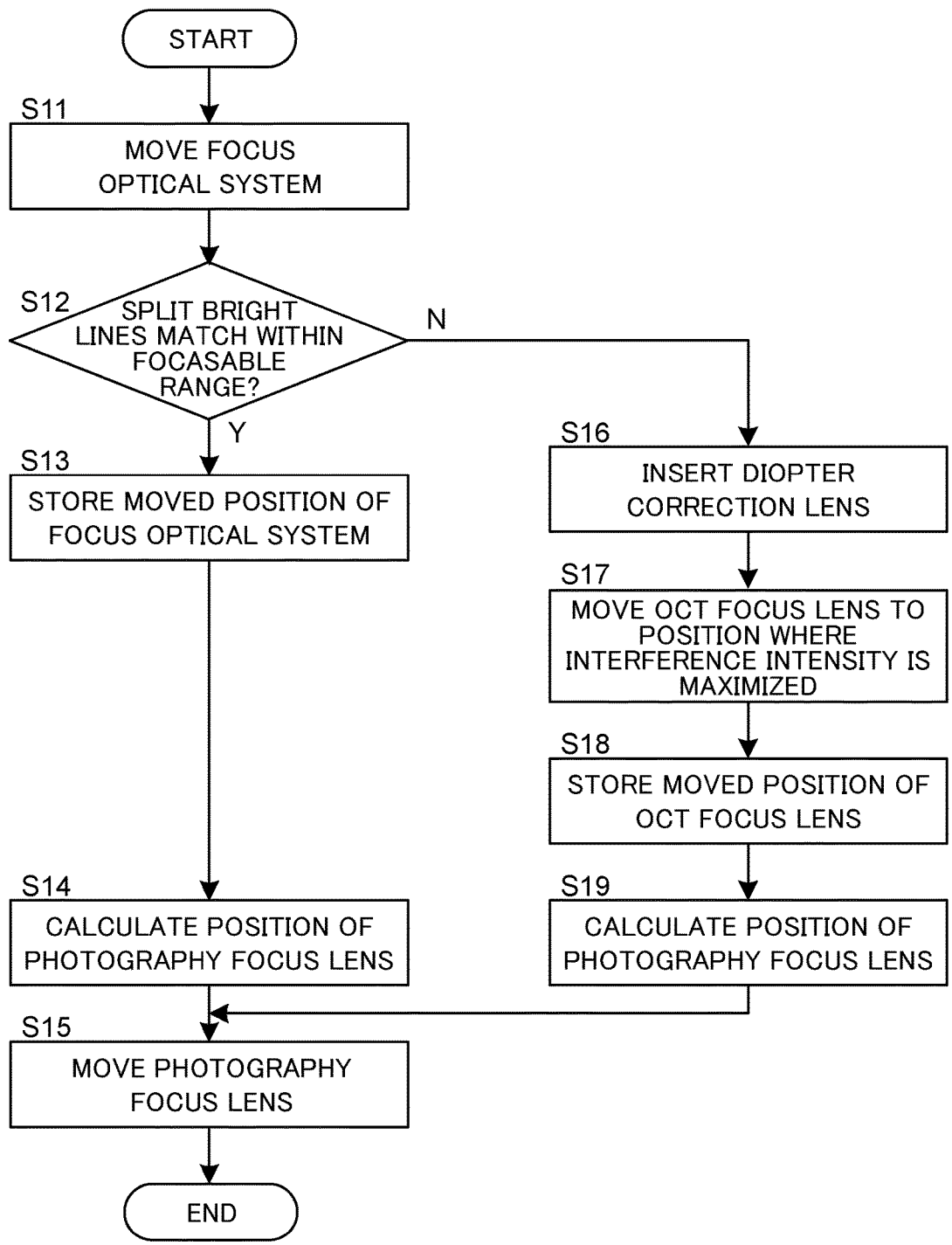
FIG. 10 is a flow chart of an operation example of the ophthalmologic imaging apparatus according to the second modification example of the embodiment.

FIG. 10 shows a flow chart of an operation example of the ophthalmologic imaging apparatus according to the second modification example of the embodiment. In this operation example, it is assumed that alignment (auto alignment) for photographing has already been performed and tracking has already been started. In addition, in this operation example, a case where the diopter correction lens 70 is to be inserted will be described.

(S11)

First, the photography focus controller 211a controls the reflection rod driver 67A to insert the reflection rod 67 into the illumination optical path. Subsequently, the photography focus controller 211a controls the focus optical system driver 60A to move the focus optical system 60 within the predetermined focusable range, and searches for a position where the split indicator images arranged in the vertical direction match (i.e., searches for a match position of the split bright lines).

(S12)

In S11, the determination unit 211e has determined whether or not a position where the split indicator images arranged in the vertical direction match has been found. When the determination unit 211e has determined that a position where the split indicator images arranged in the vertical direction match has been found (S12: Y), the operation of the ophthalmologic imaging apparatus according to the second modification example proceeds to S13. When the determination unit 211e has determined that a position where the split indicator images arranged in the vertical direction match has not been found (S12: N), the operation of the ophthalmologic imaging apparatus according to the second modification example proceeds to S16.

(S13)

When the determination unit 211e has determined that a position where the split indicator images arranged in the vertical direction match has been found (S12: Y), the main controller 411 (the photography focus controller 211a) stores the moved position of the focus optical system 60 after the movement in the storage unit 212.

(S14)

By referring to the photography focus control information 212a stored in the storage unit 212, the photography focus controller 211a calculates the position of the photography focus lens 31 from the moved position of the focus optical system 60 stored in S13.

(S15)

The photography focus controller 211a controls the photography focus driver 31A to move the photography focus lens 31 to the position obtained in S14. After the photography focus lens 31 has been moved to the focus position, the ophthalmologic imaging apparatus according to the second modification example performs photographing of the fundus Ef. This terminates the operation of the ophthalmologic imaging apparatus according to the second modification example (END).

(S16)

When the determination unit 211e has determined that a position where the split indicator images arranged in the vertical direction match has not been found (S12: N), the diopter correction controller 211f controls the correction lens driver 70A to insert the diopter correction lens 70 into the photographing optical path.

(S17)

The OCT focus controller 211b controls the ophthalmologic imaging apparatus to perform OCT measurement and controls the intensity detector 211c to start detection of the interference light LC. The OCT focus controller 211b controls the OCT focus driver 43A to move the OCT focus lens 43 up to a position where the intensity of the interference light LC detected by the intensity detector 211c is maximized.

(S18)

When the OCT focus lens 43 has been moved to the position where the intensity of the interference light LC has been maximized, the main controller 411 (the OCT focus controller 211b) stores the moved position of the OCT focus lens 43 after the movement in the storage unit 212.

(S19)

By referring to the OCT focus control information 212b stored in the storage unit 212, the photography focus controller 211a calculates the position of the photography focus lens 31 from the moved position of the OCT focus lens 43 stored in S18. Thereafter, the operation of the ophthalmologic imaging apparatus according to the second modification example proceeds to S15.

In FIG. 10, the case where the diopter correction lens 70 is automatically inserted has been described. The same manner applies for the case where the diopter correction lens 71 is automatically inserted. In addition, the ophthalmologic imaging apparatus may determine whether or not the diopter correction with the diopter correction lens 70 is satisfactory in the state where the diopter correction lens 70 has been automatically inserted into the photographing optical path. When the ophthalmologic imaging apparatus has determined that the diopter correction is not satisfactory, the diopter correction lens 71 may be automatically inserted into the photographing optical path. For example, when the intensity of the interference light detected by the intensity detector 211c in the state where the diopter correction lens has been inserted is equal to or higher than a predetermined threshold intensity, the ophthalmologic imaging apparatus can determine that the diopter correction is satisfactory.

[Effects]

The ophthalmologic imaging apparatus according to the embodiment includes a correction lens driver (e.g., the correction lens driver 70A), a determination unit (e.g., the determination unit 211e), and a diopter correction controller (e.g., the diopter correction controller 211f). The correction lens driver is configured to move the diopter correction lens. The determination unit is configured to determine whether or not the first optical system has become in focus with the first focus lens within a predetermined focusable range in the removed state. The diopter correction controller is configured to control the correction lens driver to insert the diopter correction lens into the first optical path when the determination unit has determined that the first optical system has not become in focus.

According to such a configuration, the diopter correction lens can be automatically inserted into the first optical path and the aforementioned focus control can be executed in the inserted state. Therefore, it becomes possible to automatically execute focus control using the diopter correction lens including the insertion control of the diopter correction lens.

Other Modification Examples

The configuration described above is only an example for suitably implementing the present invention. Therefore, any modification (omission, substitution, addition, etc.) within the scope of the gist of the present invention can be appropriately applied. The configuration to be applied is selected according to the purpose, for example. In addition, depending on the configuration to be applied, it is possible to obtain the actions and effects obvious to those skilled in the art and the actions and effects described in this specification.

The invention claimed is:

1. An ophthalmologic imaging apparatus, comprising:
a first optical system comprising a first focus lens movable along an optical axis of a first optical path and a diopter correction lens insertable into and removable from the first optical path, and configured to guide light from a subject's eye to a first light receiving element;
a first driver configured to move the first focus lens;
a first focus controller configured to execute mutually different focus control of the first driver in a removed state in which the diopter correction lens is removed from the first optical path and in an inserted state in which the diopter correction lens is inserted into the first optical path;
a second optical system comprising a second focus lens movable along an optical axis of a second optical path, and configured to guide the light from the subject's eye to a second light receiving element or an eyepiece;
a second driver configured to move the second focus lens; and
a second focus controller configured to determine a position of the second focus lens by executing focus control of the second driver and move the second focus lens to a focus position determined,
wherein, in the inserted state, the first focus controller determines a position of the first focus lens based on the position of the second focus lens determined by the second focus controller and moves the first focus lens to a focus position determined.

2. The ophthalmologic imaging apparatus of claim 1,
wherein the second optical system comprises an interference optical system that splits light from a light source into measurement light and reference light, projects the measurement light onto the subject's eye, and detects interference light generated from returning light of the measurement light from the subject's eye and the reference light by the second light receiving element,
the second focus lens is disposed in an optical path of the measurement light and the returning light, and
the second focus controller determines the position of the second focus lens based on the interference light detected by the interference optical system.

3. The ophthalmologic imaging apparatus of claim 2, further comprising an intensity detector configured to detect intensity of the interference light detected by the interference optical system,
wherein the second focus controller determines the position of the second focus lens to maximize the intensity of the interference light detected by the intensity detector.

4. The ophthalmologic imaging apparatus of claim 1, further comprising a storage unit configured to prestore first control information in which positions of the second focus lens are associated with positions of the first focus lens,
Wherein, in the inserted state, the first focus controller determines the position of the first focus lens based on the position of the second focus lens determined by the second focus controller and the first control information.

5. The ophthalmologic imaging apparatus of claim 1, further comprising:
a correction lens driver configured to move the diopter correction lens;
a determination unit configured to determine whether or not the first optical system has become in focus by the first focus lens within a predetermined focusable range in the removed state; and
a diopter correction controller configured to control the correction lens driver to insert the diopter correction lens into the first optical path when the determination unit has determined that the first optical system has not become in focus.

6. The ophthalmologic imaging apparatus of claim 2, further comprising a storage unit configured to prestore first control information in which positions of the second focus lens are associated with positions of the first focus lens, wherein, in the inserted state, the first focus controller determines the position of the first focus lens based on the position of the second focus lens determined by the second focus controller and the first control information.

7. The ophthalmologic imaging apparatus of claim 3, further comprising a storage unit configured to prestore first control information in which positions of the second focus lens are associated with positions of the first focus lens, wherein, in the inserted state, the first focus controller determines the position of the first focus lens based on the position of the second focus lens determined by the second focus controller and the first control information.

8. The ophthalmologic imaging apparatus of claim 1, further comprising:
an illumination optical system configured to project an illumination light beam onto the subject's eye via a third optical path coupled with the first optical path between the subject's eye and the diopter correction lens;
a focus indicator projection optical system configured to project a focus indicator onto the subject's eye via the third optical path; and
a third driver configured to move the focus indicator projection optical system along an optical axis of the third optical path,
wherein the first light receiving element receives returning light of the focus indicator from the subject's eye that has passed through the first focus lens, and
the first focus controller, in the removed state, determines the position of the first focus lens by controlling the third driver based on a position of an image of the focus indicator acquired by the first light receiving element, and moves the first focus lens to a focus position determined.

9. The ophthalmologic imaging apparatus of claim 2, further comprising:
an illumination optical system configured to project an illumination light beam onto the subject's eye via a third optical path coupled with the first optical path between the subject's eye and the diopter correction lens;
a focus indicator projection optical system configured to project a focus indicator onto the subject's eye via the third optical path; and
a third driver configured to move the focus indicator projection optical system along an optical axis of the third optical path,
wherein the first light receiving element receives returning light of the focus indicator from the subject's eye that has passed through the first focus lens, and
the first focus controller, in the removed state, determines the position of the first focus lens by controlling the third driver based on a position of an image of the focus indicator acquired by the first light receiving element, and moves the first focus lens to a focus position determined.

10. The ophthalmologic imaging apparatus of claim 3, further comprising:
an illumination optical system configured to project an illumination light beam onto the subject's eye via a third optical path coupled with the first optical path between the subject's eye and the diopter correction lens;
a focus indicator projection optical system configured to project a focus indicator onto the subject's eye via the third optical path; and
a third driver configured to move the focus indicator projection optical system along an optical axis of the third optical path,
wherein the first light receiving element receives returning light of the focus indicator from the subject's eye that has passed through the first focus lens, and
the first focus controller, in the removed state, determines the position of the first focus lens by controlling the third driver based on a position of an image of the focus indicator acquired by the first light receiving element, and moves the first focus lens to a focus position determined.

11. The ophthalmologic imaging apparatus of claim 4, further comprising:
an illumination optical system configured to project an illumination light beam onto the subject's eye via a third optical path coupled with the first optical path between the subject's eye and the diopter correction lens;
a focus indicator projection optical system configured to project a focus indicator onto the subject's eye via the third optical path; and
a third driver configured to move the focus indicator projection optical system along an optical axis of the third optical path,
wherein the first light receiving element receives returning light of the focus indicator from the subject's eye that has passed through the first focus lens, and
the first focus controller, in the removed state, determines the position of the first focus lens by controlling the third driver based on a position of an image of the focus indicator acquired by the first light receiving element, and moves the first focus lens to a focus position determined.

12. The ophthalmologic imaging apparatus of claim 1, further comprising:
a correction lens driver configured to move the diopter correction lens;
a determination unit configured to determine whether or not the first optical system has become in focus by the first focus lens within a predetermined focusable range in the removed state; and
a diopter correction controller configured to control the correction lens driver to insert the diopter correction lens into the first optical path when the determination unit has determined that the first optical system has not become in focus.

13. The ophthalmologic imaging apparatus of claim 2, further comprising:
a correction lens driver configured to move the diopter correction lens;
a determination unit configured to determine whether or not the first optical system has become in focus by the first focus lens within a predetermined focusable range in the removed state; and
a diopter correction controller configured to control the correction lens driver to insert the diopter correction lens into the first optical path when the determination unit has determined that the first optical system has not become in focus.

14. The ophthalmologic imaging apparatus of claim 3, further comprising:
a correction lens driver configured to move the diopter correction lens;
a determination unit configured to determine whether or not the first optical system has become in focus by the first focus lens within a predetermined focusable range in the removed state; and
a diopter correction controller configured to control the correction lens driver to insert the diopter correction lens into the first optical path when the determination unit has determined that the first optical system has not become in focus.

15. The ophthalmologic imaging apparatus of claim 4, further comprising:
a correction lens driver configured to move the diopter correction lens;
a determination unit configured to determine whether or not the first optical system has become in focus by the first focus lens within a predetermined focusable range in the removed state; and
a diopter correction controller configured to control the correction lens driver to insert the diopter correction lens into the first optical path when the determination unit has determined that the first optical system has not become in focus.

16. An ophthalmologic imaging apparatus, comprising:
a first optical system comprising a first focus lens movable along an optical axis of a first optical path and a diopter correction lens insertable into and removable from the first optical path, and configured to guide light from a subject's eye to a first light receiving element;
a first driver configured to move the first focus lens; and
a first focus controller configured to execute mutually different focus control of the first driver in a removed state in which the diopter correction lens is removed from the first optical path and in an inserted state in which the diopter correction lens is inserted into the first optical path;

an illumination optical system configured to project an illumination light beam onto the subject's eye via a third optical path coupled with the first optical path between the subject's eye and the diopter correction lens;

a focus indicator projection optical system configured to project a focus indicator onto the subject's eye via the third optical path; and a third driver configured to move the focus indicator projection optical system along an optical axis of the third optical path, wherein the first light receiving element receives returning light of the focus indicator from the subject's eye that has passed through the first focus lens, and the first focus controller, in the removed state, determines the position of the first focus lens by controlling the third driver based on a position of an image of the focus indicator acquired by the first light receiving element, and moves the first focus lens to a focus position determined.

17. The ophthalmologic imaging apparatus of claim 16, further comprising:

a storage unit configured to prestore second control information in which a position of the focus indicator projection optical system at which the position of the image of the focus indicator matches a predetermined position is associated with a position of the first focus lens, and correction information for correcting the second control information, wherein the first focus controller determines the position of the first focus lens based on the second control information and moves the first focus lens to a focus position determined in the removed state, and determines a new position of the first focus lens by correcting the position of the first focus lens stored in the storage unit based on the correction information and moves the first focus lens to the new position in the inserted state.

18. The ophthalmologic imaging apparatus of claim 16, further comprising:

a correction lens driver configured to move the diopter correction lens;

a determination unit configured to determine whether or not the first optical system has become in focus by the first focus lens within a predetermined focusable range in the removed state; and a diopter correction controller configured to control the correction lens driver to insert the diopter correction lens into the first optical path when the determination unit has determined that the first optical system has not become in focus.

19. The ophthalmologic imaging apparatus of claim 17, further comprising:

a correction lens driver configured to move the diopter correction lens;

a determination unit configured to determine whether or not the first optical system has become in focus by the first focus lens within a predetermined focusable range in the removed state; and a diopter correction controller configured to control the correction lens driver to insert the diopter correction lens into the first optical path when the determination unit has determined that the first optical system has not become in focus.

* * * * *

UNITED STATES PATENT AND TRADEMARK OFFICE
CERTIFICATE OF CORRECTION

PATENT NO. : 10,448,827 B2
APPLICATION NO. : 15/575850
DATED : October 22, 2019
INVENTOR(S) : Okuda Page 1 of 1

It is certified that error appears in the above-identified patent and that said Letters Patent is hereby corrected as shown below:

On the Title Page

Item (54), Please delete "(54) OPHTHALMOLOGIC IMAGING APPARATUS " and insert -- Ophthalmologic imaging apparatus --.

Signed and Sealed this
Twenty-first Day of January, 2020

Andrei Iancu
*Director of the United States Patent and Trademark Office*